(12) United States Patent
Makower et al.

(10) Patent No.: US 8,474,462 B2
(45) Date of Patent: Jul. 2, 2013

(54) TONGUE RETAINING ORAL APPLIANCE

(75) Inventors: Joshua Makower, Los Altos, CA (US); James Blackburn Joslin, San Francisco, CA (US); Michael Strasser, San Francisco, CA (US); Clinton N. Slone, San Francisco, CA (US); Earl A. Bright, II, Los Altos, CA (US); Marc Spinali, Danville, CA (US); Richard A. Carlson, San Jose, CA (US)

(73) Assignee: Sleepy, Inc., Mountain View, CA (US)

( * ) Notice: Subject to any disclaimer, the term of this patent is extended or adjusted under 35 U.S.C. 154(b) by 0 days.

(21) Appl. No.: 13/512,679

(22) PCT Filed: Jun. 7, 2011

(86) PCT No.: PCT/US2011/039475
§ 371 (c)(1),
(2), (4) Date: May 30, 2012

(87) PCT Pub. No.: WO2011/156396
PCT Pub. Date: Dec. 15, 2011

(65) Prior Publication Data
US 2013/0068235 A1       Mar. 21, 2013

Related U.S. Application Data

(60) Provisional application No. 61/352,298, filed on Jun. 7, 2010, provisional application No. 61/406,508, filed on Oct. 25, 2010.

(51) Int. Cl.
*A61C 5/14* (2006.01)
(52) U.S. Cl.
USPC .......................... 128/860; 128/848; 602/902

(58) Field of Classification Search
USPC .......... 128/846, 848, 857, 859–862; 602/902; 433/6, 7, 18, 20–22, 140
See application file for complete search history.

(56) References Cited

U.S. PATENT DOCUMENTS

| 3,132,647 A | 5/1964 | Giuseppe |
| 3,277,892 A | 10/1966 | William |

(Continued)

FOREIGN PATENT DOCUMENTS

| EP | 2181678 A1 | 5/2010 |
| WO | WO9519155 A1 | 7/1995 |

(Continued)

OTHER PUBLICATIONS

"Practice Parameters for the Treatment of Snoring and Obstructive Sleep Apnea with Oral Appliances: An Update for 2005", Kushida; Morgenthaler; Littner et al., Sleep, 2006, 29:240-243.

(Continued)

*Primary Examiner* — Patricia Bianco
*Assistant Examiner* — Raymond E Harris
(74) *Attorney, Agent, or Firm* — Fish & Richardson P.C.

(57) ABSTRACT

An oral appliance includes a frame for mounting to a user's teeth and a tongue contacting retaining member extending from the frame and configured in use to limit movement of the tongue toward the user's throat when the user is exercising or sleeping to maintain an open air passageway. The retaining member is positioned relative to the frame such that in use the retaining member contacts the tongue in a zone behind the second molars and in front of the pharyngeal reflex region of the tongue. The retaining member is further configured to lightly contact the tongue, and to apply a restraining force to the tongue as the tongue begins to move toward the user's throat during exercise or as the user falls asleep.

20 Claims, 56 Drawing Sheets

U.S. PATENT DOCUMENTS

| | | | |
|---|---|---|---|
| 3,312,216 A | | 4/1967 | Melvin |
| 3,871,370 A | | 3/1975 | McDonald |
| 4,169,473 A | * | 10/1979 | Samelson ..................... 128/848 |
| 4,273,530 A | | 6/1981 | Broussard |
| 4,299,568 A | | 11/1981 | Crowley |
| 4,304,227 A | * | 12/1981 | Samelson ..................... 128/848 |
| 4,468,196 A | | 8/1984 | Keller |
| 4,669,459 A | | 6/1987 | Spiewak et al. |
| 4,676,240 A | * | 6/1987 | Gardy .......................... 128/848 |
| 4,901,737 A | | 2/1990 | Toone |
| 4,976,614 A | | 12/1990 | Tepper |
| 5,052,409 A | | 10/1991 | Tepper |
| 5,096,416 A | | 3/1992 | Hulsink |
| 5,376,001 A | | 12/1994 | Tepper |
| 5,465,734 A | * | 11/1995 | Alvarez et al. ................ 128/848 |
| 5,499,633 A | | 3/1996 | Fenton |
| 5,580,243 A | | 12/1996 | Bloore |
| 5,607,300 A | * | 3/1997 | Tepper ............................. 433/6 |
| 5,692,521 A | | 12/1997 | Leasure-Nelson |
| 5,752,822 A | | 5/1998 | Robson |
| 5,848,891 A | | 12/1998 | Eckhart et al. |
| 5,865,619 A | | 2/1999 | Cross et al. |
| 5,915,385 A | | 6/1999 | Hakimi |
| 6,408,852 B2 | | 6/2002 | Tielemans |
| 6,467,484 B1 | * | 10/2002 | De Voss ....................... 128/848 |
| 6,766,802 B1 | | 7/2004 | Keropian |
| 6,976,491 B2 | * | 12/2005 | D'Agosto ..................... 128/859 |
| 7,073,506 B2 | | 7/2006 | Robertson et al. |
| 7,237,554 B2 | | 7/2007 | Conrad et al. |
| 7,367,340 B2 | | 5/2008 | Nelson et al. |
| 7,451,767 B2 | | 11/2008 | Keropian |
| 7,607,439 B2 | | 10/2009 | Li |
| 7,658,192 B2 | | 2/2010 | Harrington |
| 7,721,741 B2 | | 5/2010 | Thornton |
| 7,730,888 B2 | | 6/2010 | Dunlap |
| 7,730,890 B2 | | 6/2010 | Enoch |
| 7,730,891 B2 | | 6/2010 | Lamberg |
| 8,127,769 B2 | * | 3/2012 | Walker .......................... 128/848 |
| 2006/0078840 A1 | | 4/2006 | Robson |
| 2006/0110698 A1 | | 5/2006 | Robson |
| 2006/0130850 A1 | | 6/2006 | Chen |
| 2006/0289013 A1 | | 12/2006 | Keropian |
| 2007/0224567 A1 | | 9/2007 | Robson |
| 2008/0041396 A1 | | 2/2008 | Lucker |
| 2008/0210244 A1 | | 9/2008 | Keropian |
| 2009/0056724 A1 | | 3/2009 | Keropian |
| 2009/0120446 A1 | | 5/2009 | Vaska et al. |
| 2009/0120448 A1 | * | 5/2009 | Keropian ...................... 128/848 |
| 2009/0126742 A1 | * | 5/2009 | Summer ........................ 128/848 |
| 2009/0165803 A1 | | 7/2009 | Bhat et al. |
| 2009/0178684 A1 | * | 7/2009 | Greenburg .................... 128/848 |
| 2009/0241969 A1 | | 10/2009 | Walker |
| 2010/0000551 A1 | | 1/2010 | Li |
| 2010/0043804 A1 | | 2/2010 | Razmovski |
| 2010/0099054 A1 | | 4/2010 | Smernoff |
| 2010/0132720 A1 | | 6/2010 | Razmovski |
| 2010/0139666 A1 | | 6/2010 | Bonnaure |
| 2010/0184566 A1 | | 7/2010 | Munehiro |
| 2011/0259346 A1 | | 10/2011 | Tsuiki et al. |
| 2011/0262881 A1 | | 10/2011 | Mauclaire |
| 2012/0031410 A1 | | 2/2012 | Jackson |
| 2012/0031411 A1 | | 2/2012 | Horian |
| 2012/0073581 A1 | | 3/2012 | Martinez |

FOREIGN PATENT DOCUMENTS

| | | |
|---|---|---|
| WO | WO2004021869 A2 | 3/2004 |
| WO | WO2009096889 A1 | 8/2009 |
| WO | WO2009158424 A1 | 12/2009 |
| WO | WO2010062952 A1 | 6/2010 |

OTHER PUBLICATIONS

"Oral Appliances for Snoring and Obstructive Sleep Apnea: A Review." Ferguson, Kathleen A., Cartwright, Rosalind, Rogers, Robert, Schmidt-Nowara, Wolfgang. Sleep 29.2 (2006): 244-262.

"Machining for Air", Peter Zelinski. MMS Online, Jun. 2007, 3 pages.

Authorized officer Kim, Myeong Hee, International Search Report/Written Opinion in PCT/US2001/039475 mailed Feb. 20, 2012, 13 pages.

* cited by examiner

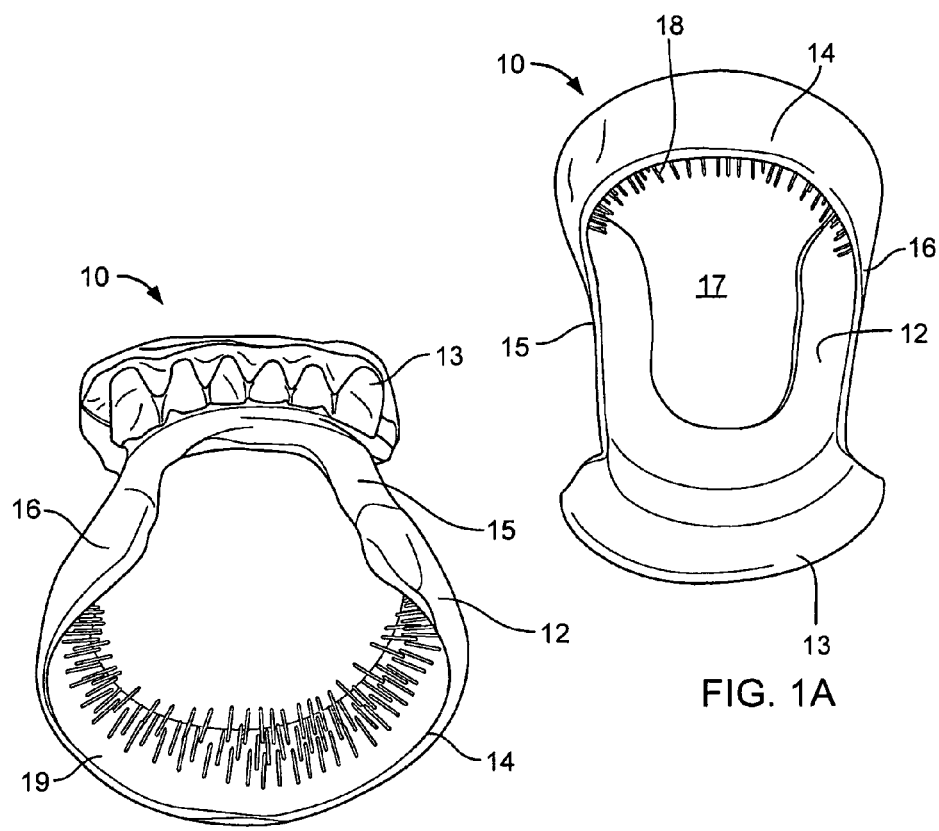
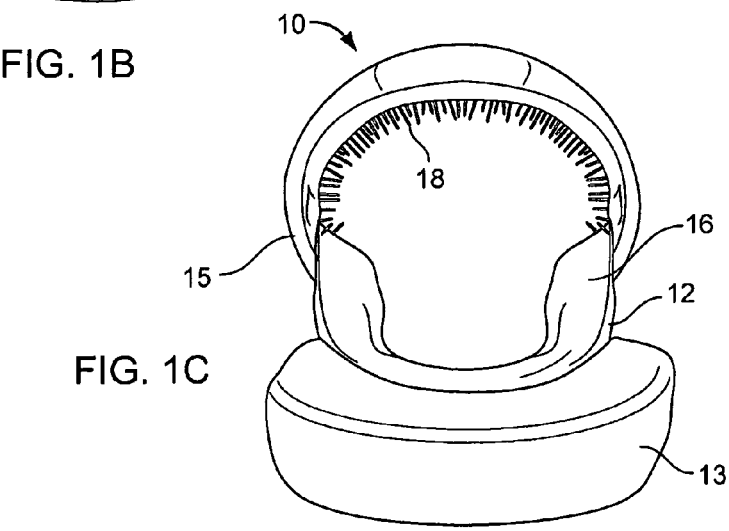
FIG. 1A
FIG. 1B
FIG. 1C

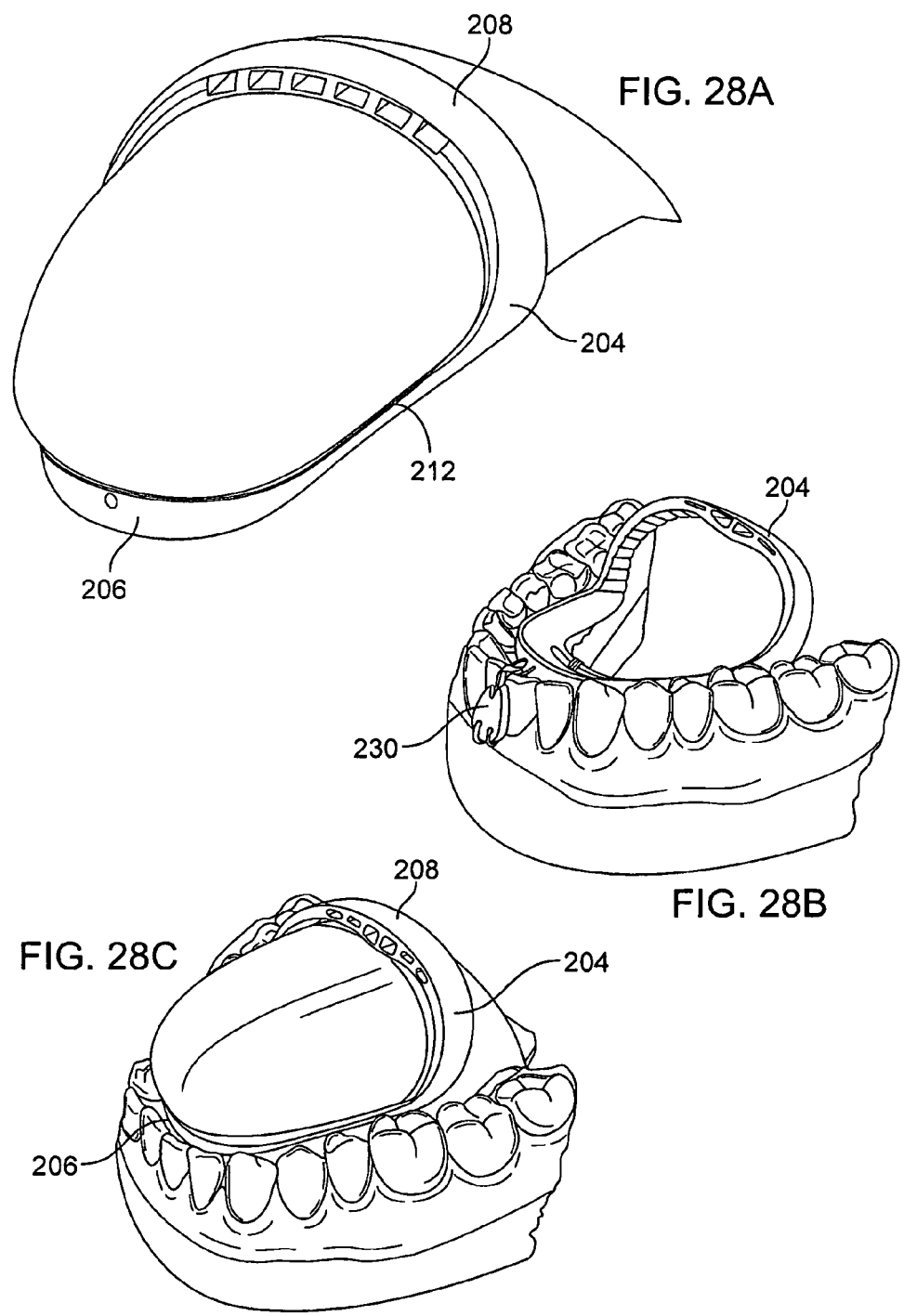

TONGUE RETAINING ORAL APPLIANCE

CROSS-REFERENCE TO RELATED APPLICATION

This application is a national stage application of PCT/US2011/039475, filed Jun. 7, 2011, and titled "TONGUE RETAINING ORAL APPLIANCE", which claims priority to U.S. Provisional Application No. 61/352,298, filed Jun. 7, 2010, and titled "TONGUE RETAINING ORAL APPLIANCE," and U.S. Provisional Application No. 61/406,508, filed Oct. 25, 2010, and titled "TONGUE RETAINING ORAL APPLIANCE", the entire contents of which are incorporated herein by reference.

TECHNICAL FIELD

This description relates to an oral appliance for retaining the tongue forward to open the airway during exercise or sleep.

BACKGROUND

Snoring is vibration caused by a narrowed or constricted airway during sleep. Narrowing or constriction of the airway can happen for many reasons including large tonsils, nasal congestion, a long soft palate or uvula, excessive flabby tissue, and cartilage deformities in the nose or nasal structure. Snoring can also be accompanied by sleep apnea. People with sleep apnea are deprived of oxygen due to a complete blockage of the airways. Obstructive sleep apnea (OSA) is the most common type of sleep apnea and is caused by an obstruction, which stops the air flow in the nose and mouth. A common cause of snoring and OSA is the tongue muscle relaxing too much during sleep, blocking the airways.

SUMMARY

A tongue retaining oral appliance includes a frame for connecting to a user's teeth and a tongue contacting retaining member extending from the frame and configured in use to limit movement of the tongue toward the user's throat when the user is exercising or sleeping to maintain an open air passageway. The retaining member is positioned relative to the frame such that in use the retaining member contacts the tongue in a zone behind the second molars and in front of the pharyngeal reflex region of the tongue. In some embodiments, the retaining member is further configured to lightly contact the tongue with less than about 0.1 PSI of pressure, and to apply a restraining force to the tongue as the tongue begins to move toward the user's throat during exercise or as the user falls asleep, particularly for users who suffer from snoring or obstructive sleep apnea.

In one aspect, a device for receipt in a user's mouth includes a tongue engagement element having a front region, a rear region, and side regions that define an opening for receiving a user's tongue. The side regions extend back and outward from the front region to the rear region such that the rear region is wider than the front region.

Embodiments of this aspect may include the front region having an upper surface and the rear region having a lower surface. The rear region extends upward relative to the front region such that the lower surface is spaced from the upper surface to receive the user's tongue therebetween.

Additional embodiments may include one or more of the following features.

The rear region includes tongue retaining structures. The element is shaped such that when placed in a user's mouth, the rear region extends over the user's tongue to rest on the tongue and the front region extends under the user's tongue. The element does not interfere with the user's normal bite. The side regions extend along the floor of the user's mouth cavity under the tongue.

The rear region is generally arch shaped with piers that include tongue retaining structures, and the tongue engagement element is shaped such that when placed in a user's mouth, the rear region curves over the user's tongue to engage the sides of the user's tongue with the tongue retaining formations, and the front region extends under the user's tongue.

The tongue engagement element has a length, L, that is greater than a width, W1. The lower surface is spaced from the upper surface at least about 13 mm. The front, rear, and side regions form a loop.

According to another aspect, a method for treating sleep apnea includes placing a tongue engagement element under a front region of a tongue and over a rear region of the tongue. The tongue engagement element acts to resist rearward motion of the tongue.

Embodiments of this aspect may include one or more of the following features.

Tongue retaining structures of the element engaging the tongue acting to resist rearward motion of the tongue. The tongue engaging element is placed without interfering with the user's normal bite. Side regions of the tongue engagement element extend along the floor of the user's mouth cavity under the tongue. The rear region is generally arch shaped with piers that include tongue retaining structures engaging the tongue. The tongue engagement element has a length, L, that is greater than a width, W.

According to another aspect, a device for receipt in a user's mouth includes a tongue engagement element configured to extend over and under the tongue, an anchor, and a member connecting the element and the anchor such that with the tongue engagement element extending over and under the tongue and the member positioned between two teeth, the member resides spaced from the gum line and the anchor resides between the user's teeth and user's lip to secure the tongue engagement element in position in the user's mouth.

According to another aspect, a method of securing a tongue engagement element in a user's mouth includes placing a tongue engagement element under a front region of a tongue and over a rear region of the tongue, placing a member connecting the tongue engagement element to an anchor between two teeth, and positioning the anchor between the user's teeth and the user's lip.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1a-1c are top, bottom and front views, respectively, of a tongue retaining oral appliance.

FIG. 26b is a bottom view of the tongue retaining oral appliance of FIG. 26a.

FIGS. 28a-28d illustrate the tongue retaining oral appliance of FIG. 27a in position.

FIGS. 29a-29h illustrate an anchor device of the tongue retaining oral appliance of FIG. 27a.

FIGS. 30 and 31 illustrate tongue engaging structures of the tongue retaining oral appliance of FIG. 27a.

FIGS. 32a and 32b illustrate an alternative embodiment of a tensioning mechanism of the tongue retaining oral appliance of FIG. 27a.

FIGS. 33a and 33b illustrate additional alternative embodiments of a tensioning mechanism of the tongue retaining oral appliance of FIG. 27a.

DETAILED DESCRIPTION

Figure 1D:
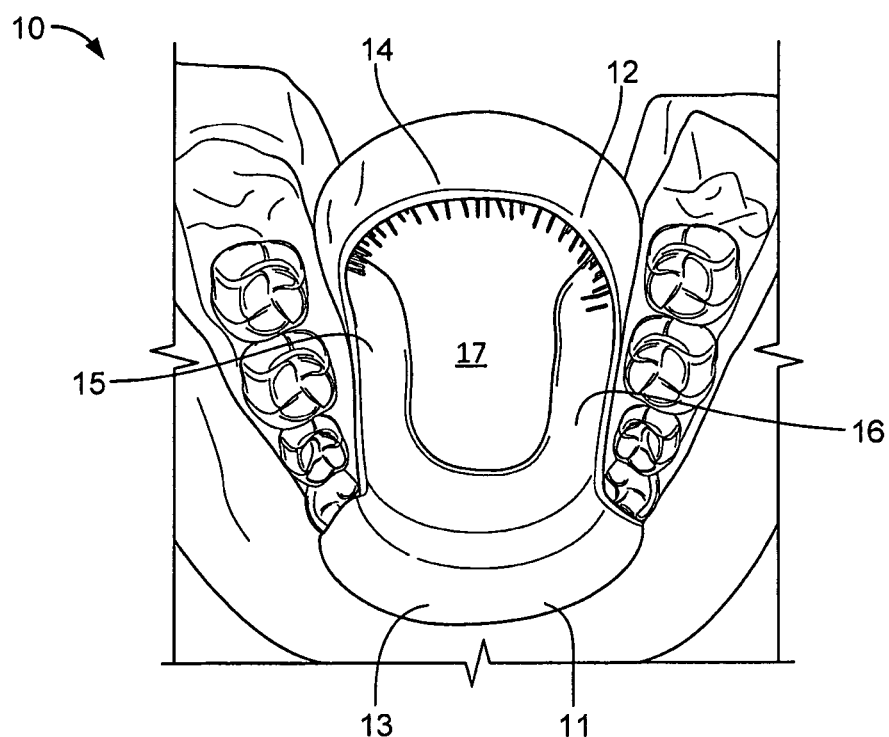
FIG. 1d shows the tongue retaining oral appliance in position over bottom teeth of a teeth mold.
Figure 1E:
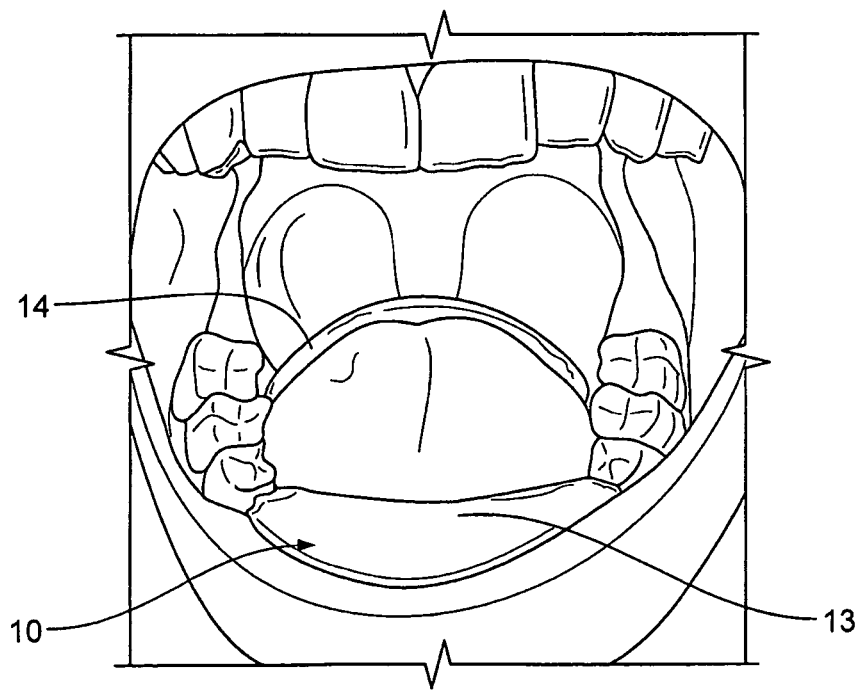
FIG. 1e is an illustration of the tongue retaining oral appliance in position within a user's mouth.

A tongue retaining oral appliance has a tongue contacting member that limits movement of the tongue toward the user's throat to maintain an open air passageway when the user is exercising or sleeping, such as to minimize or eliminate snoring and/or treat obstructive sleep apnea. To promote user comfort, the tongue contacting member has a small contact area, and contacts the tongue in a region of the tongue that limits the gag reflex, limits inducing salivation, and allows the tongue to move during swallowing to contact the upper palate. To further promote user comfort, in some embodiments, the tongue contacting member contacts the tongue lightly, that is does not depress the tongue, when the user is falling asleep, and applies a restraining force to the tongue as the tongue begins to move toward the user's throat as the user falls asleep. For use during exercise, the tongue contacting member can depress the tongue more if needed. The oral appliance can be sold over-the-counter as it does not require custom fitting by a professional.

Referring to FIGS. 1a-1e, an oral appliance 10 includes a frame 12 with a mandibular attachment 13 for attaching the frame 12 to the bottom front teeth 11 of a user. The frame 12 has a tongue contacting, retaining band 14 with spaced, angled microfilament bristles 18 on a tongue contacting side 19 of the band 14, and extensions 15, 16 that connect the mandibular attachment 13 and the band 14. The bristles 18 are spaced apart about 1.5 mm and are angled toward the front of the mouth at about a 45 degree angle to the band 14. The microfilament bristles 18 can be molded from, for example, silicone thermoplastic elastomer (TPE), Polyethylene terephthalate (PET), nylon, or Low-density polyethylene (LDPE). The frame 12 defines a central aperture 17 through which the user's tongue extends.

In use, the user places the appliance 10 in their mouth with the mandibular attachment 13 placed on their lower front teeth and their tongue lying through aperture 17. With the tongue in its-normal position prior to falling asleep, in one embodiment, the band 14 lightly touches the top surface of the tongue thus limiting any discomfort caused by wearing the appliance 10. After falling asleep, the tongue of a sufferer of obstructive sleep apnea can slip backward in the mouth toward the user's throat. When this happens, the angled bristles 18 of the band 14 engage the top surface of the tongue more firmly, applying a forward acting force to the tongue, that is, predominantly a shear force rather than a vertically directed force, to limit backward movement of the tongue and thus keep the airway open.

The frame 12 can be made from, for example, FDA silicone, stainless steel, dental acrylic, thermoplastic elastomer (TPE), Polyethylene terephthalate (PET), and Low-density polyethylene (LDPE). The band 14 can include an embedded wire (not shown) to add rigidity to the tongue retainer. The aperture 17 is contoured to fit the frenulum on the underside of the tongue. The mandibular attachment 13 can be molded to the user's teeth, for example, by forming the mandibular attachment 13 with a heat sensitive polymer that can be heated by the user and placed over the front teeth 11 to mold the mandibular attachment 13. Alternatively, the appliance can be custom fit by a professional.

Figure 2A:
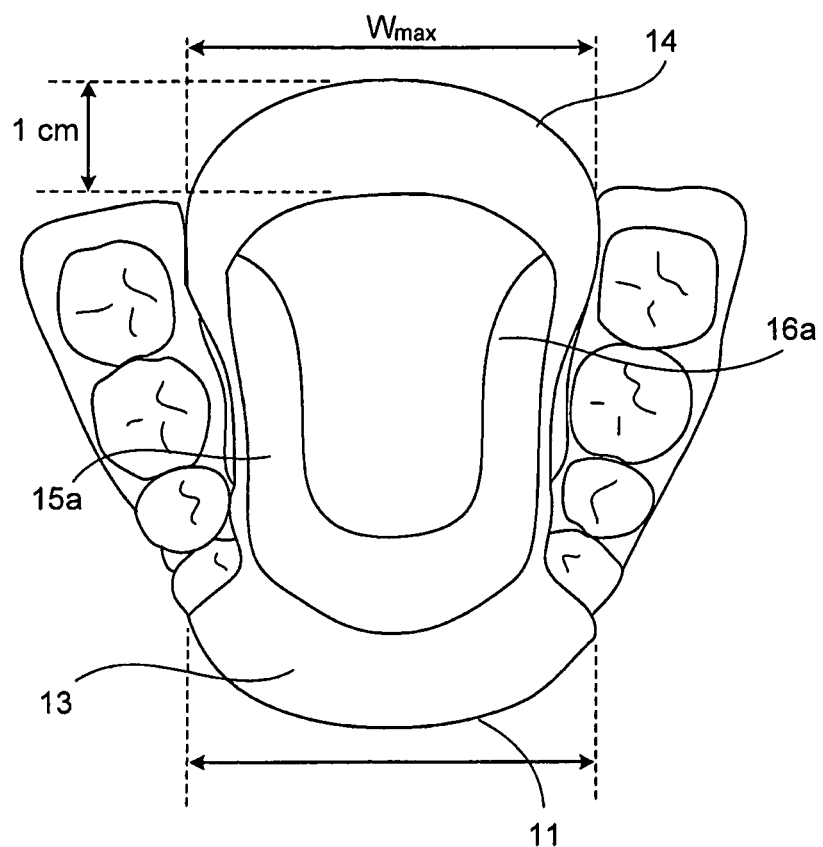
FIGS. 2a-2d illustrate the sizing and positioning of the tongue retaining oral appliance.
Figure 2B:
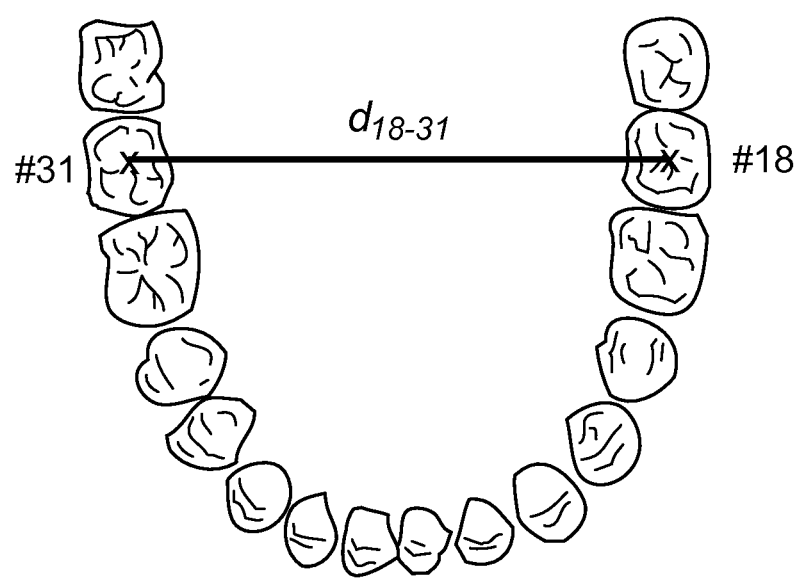

The appliance 10 can be provided, for example, in three standard sizes—small, medium and large. The user's size can be determined by the spacing, $d_{18-31}$, between the second molars #18, 31 (FIG. 2a), which the user can self measure. As shown in FIG. 2b, the maximum width, Wmax, of the appliance is related to the spacing between the second molars and is limited by the width of the inside of the mandibular dental arch. The retaining band 14 is, for example, about 1 cm wide. The mandibular attachment 13 is sized to cover the lower front teeth #22-27. The extensions 15, 16 are contoured to closely match the contour of the lingual frenulum, and include flexible sections 15a, 16a that fit under the tongue and allow the tongue retaining band 14 to move vertically with the tongue.

Figure 2C:
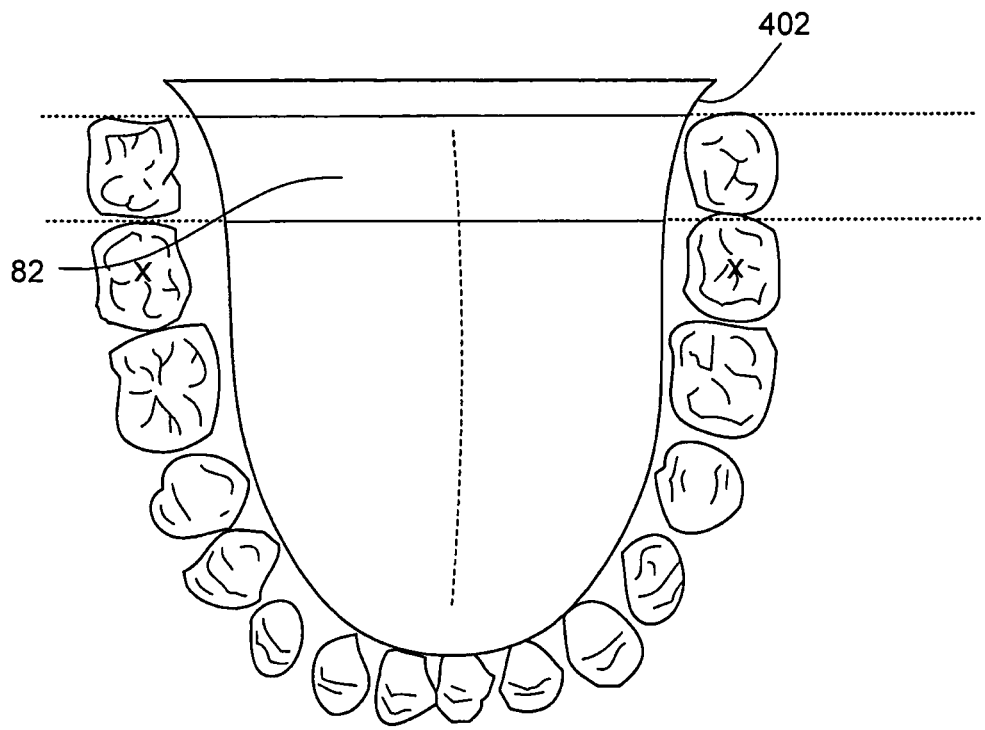
Figure 2D:
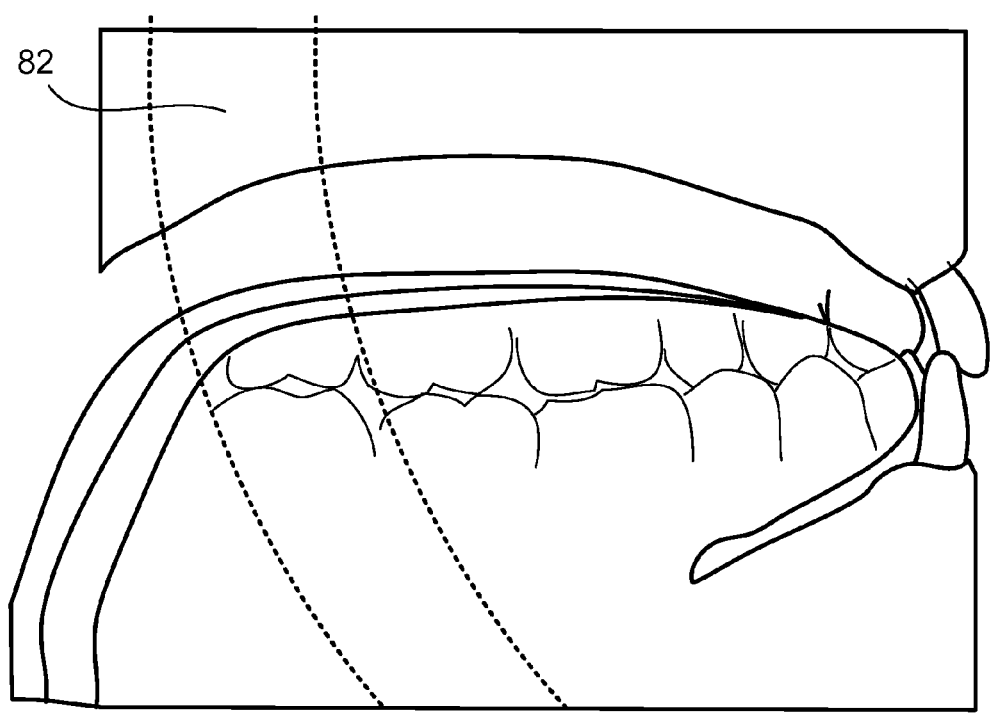
Figure 3A:
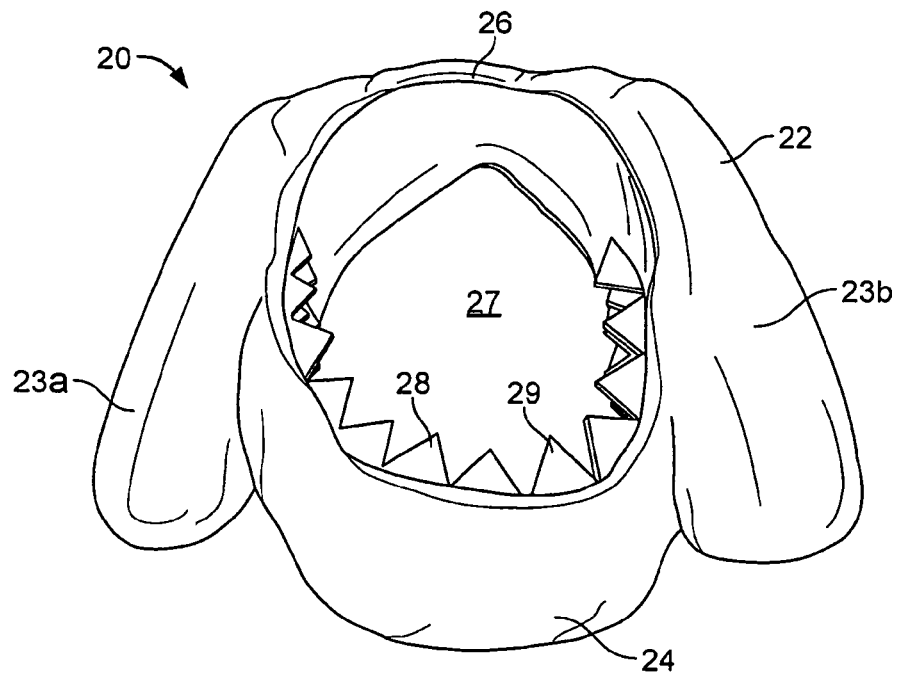
FIGS. 3a and 3b are top and bottom views, respectively, of a tongue retaining oral appliance that is mounted to the lower side teeth.
Figure 3B:
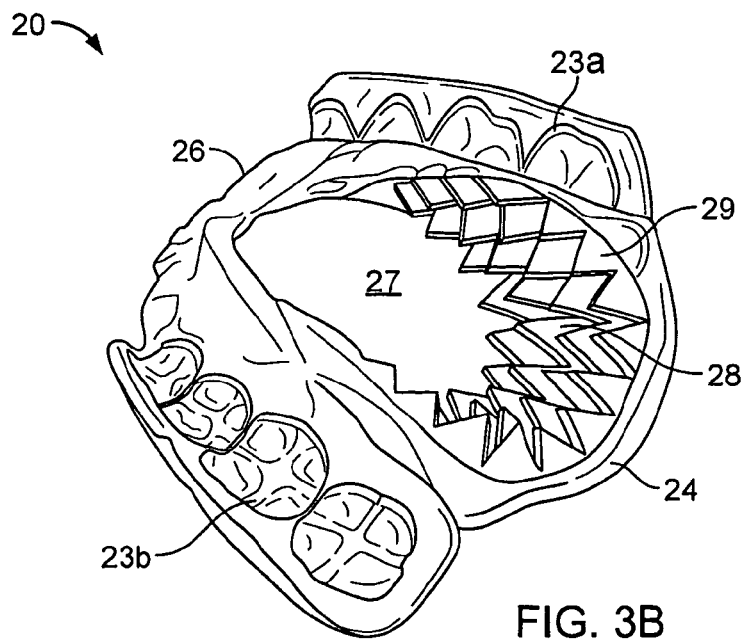
Figure 3C:
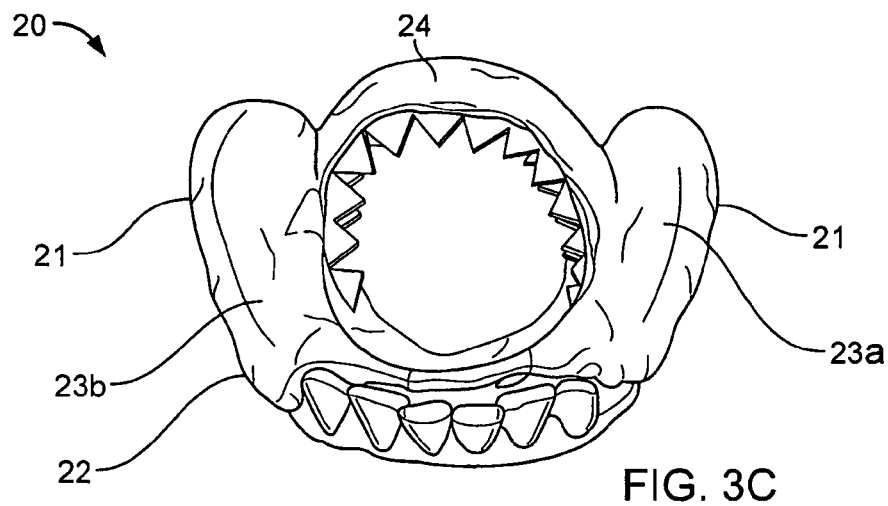
FIG. 3c shows the tongue retaining oral appliance of FIG. 3a in position over bottom teeth of a teeth mold.
Figure 3D:
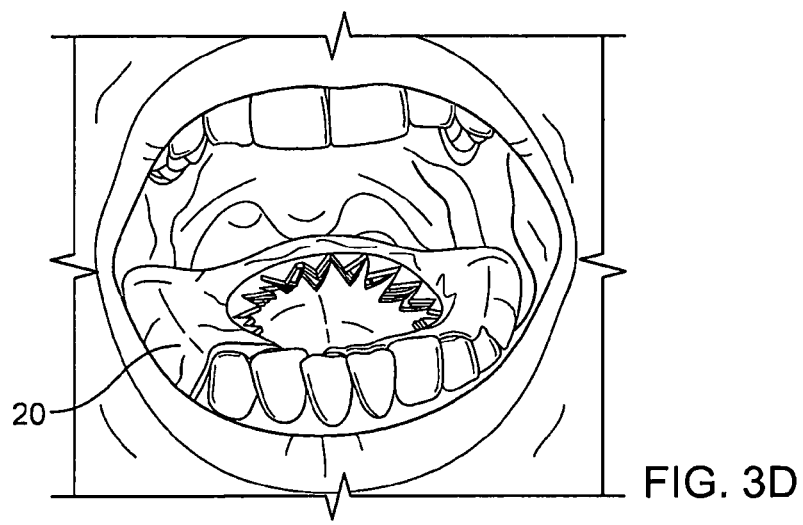
FIGS. 3d and 3e illustrate the tongue retaining oral appliance of FIG. 3a in position within a user's mouth.
Figure 3E:
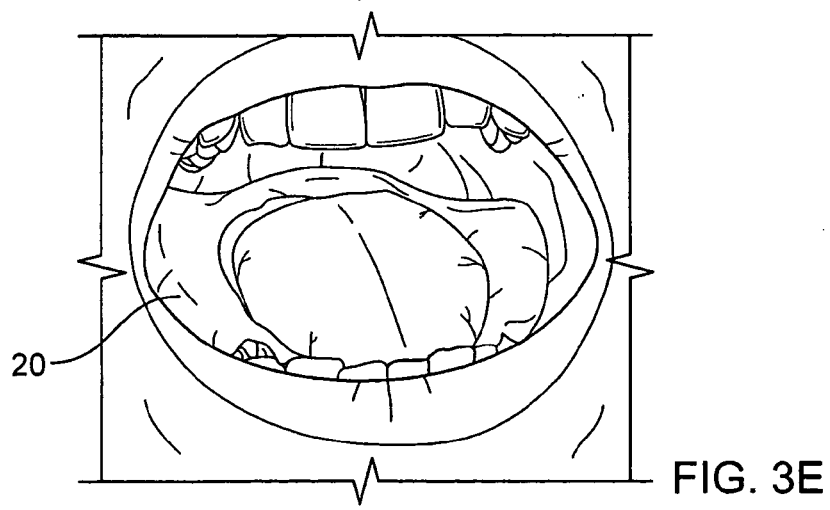

As illustrated in FIGS. 2c and 2d, the pharyngeal reflex begins behind the lower molars in the region around the vallate papillae 402 of the tongue. In use, the retaining band 14 contacts the user's tongue behind the second molars #18, 31 and in front of the pharyngeal reflex in a zone 82 in the back of the tongue corresponding to the last row of molars (the wisdom teeth).

Referring to FIGS. 3a-3e, according to another embodiment, an oral appliance 20 includes a frame 22 with mandibular attachments 23a, 23b for attaching the frame 22 to the side teeth 21 of a user. The mandibular attachments 23a, 23b are molded to the user's teeth. The frame 22 has a tongue contacting, retaining band 24 that connects the mandibular attachments 23a, 23b and contacts the tongue in zone 82. The retaining band 24 includes angled silicone fins that resemble shark-teeth 28 on a tongue contacting side 29 of the band 24. Spanning between the mandibular attachments 23a, 23b along the inside of the front teeth is a bridge 26. To provide added comfort, the bridge 26 does not extend over the teeth. The frame 22 defines a central aperture 27 through which the user's tongue extends. Rather than shark-teeth shaped edges 28, the band 24 can include the bristles of FIG. 1, and the band 14 of the embodiment of FIG. 1 can include shark-teeth shaped edges rather than bristles.

Figure 4A:
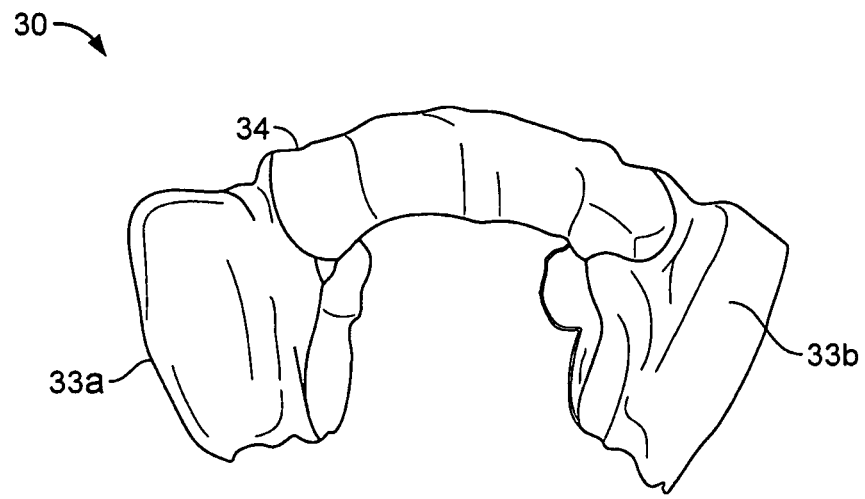
FIGS. 4a and 4b illustrate a tongue retaining oral appliance that mounts to only the rear molars.
Figure 4B:
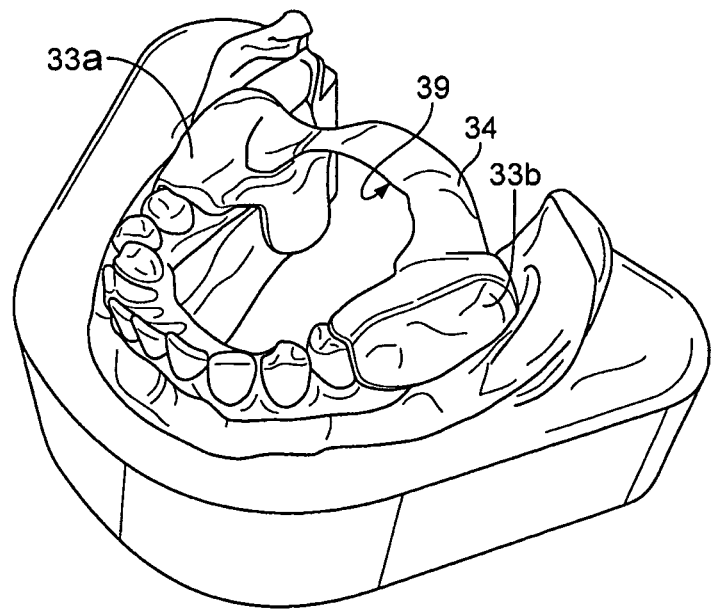

Referring to FIGS. 4a and 4b, in another embodiment, rather than having the mandibular attachments connected by a bridge that runs along the front teeth, an oral appliance 30 has mandibular attachments 33a, 33b that are molded over the back molars. The mandibular attachments 33a, 33b are connected by a retaining band 34 that in use contacts the top of the user's tongue. The retaining band 34 can include shark-teeth shaped edges, bristles, or other retaining surfaces, discussed below, on a tongue contacting side 39 of the band 34.

Figure 5:
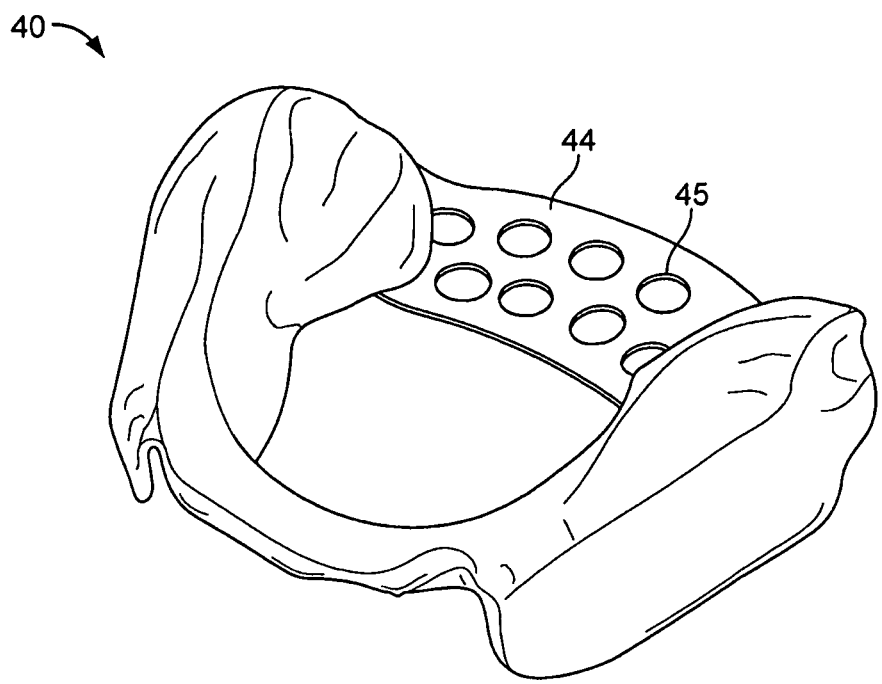
FIGS. 5-7 are top views of tongue retaining oral appliances having perforated retaining bands.
Figure 6:
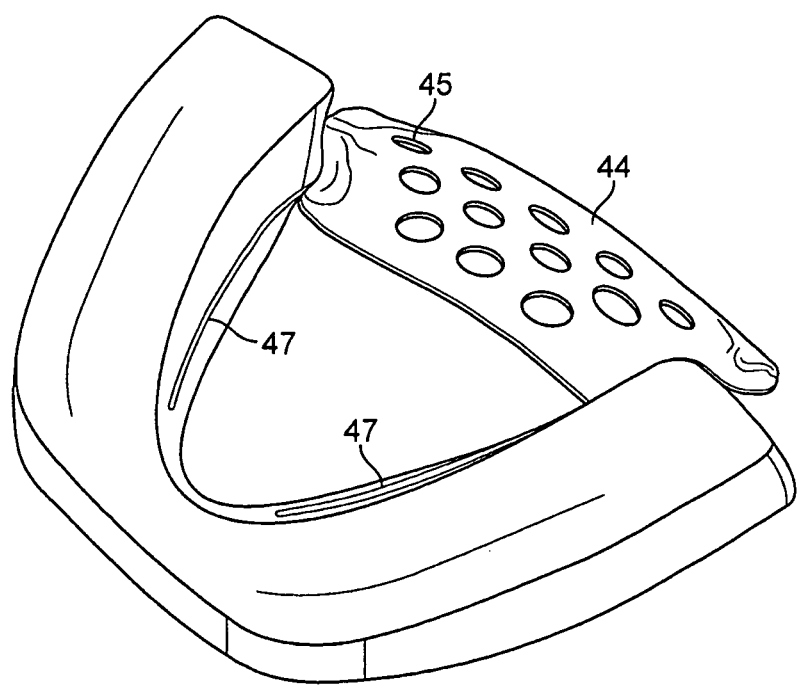
Figure 7:
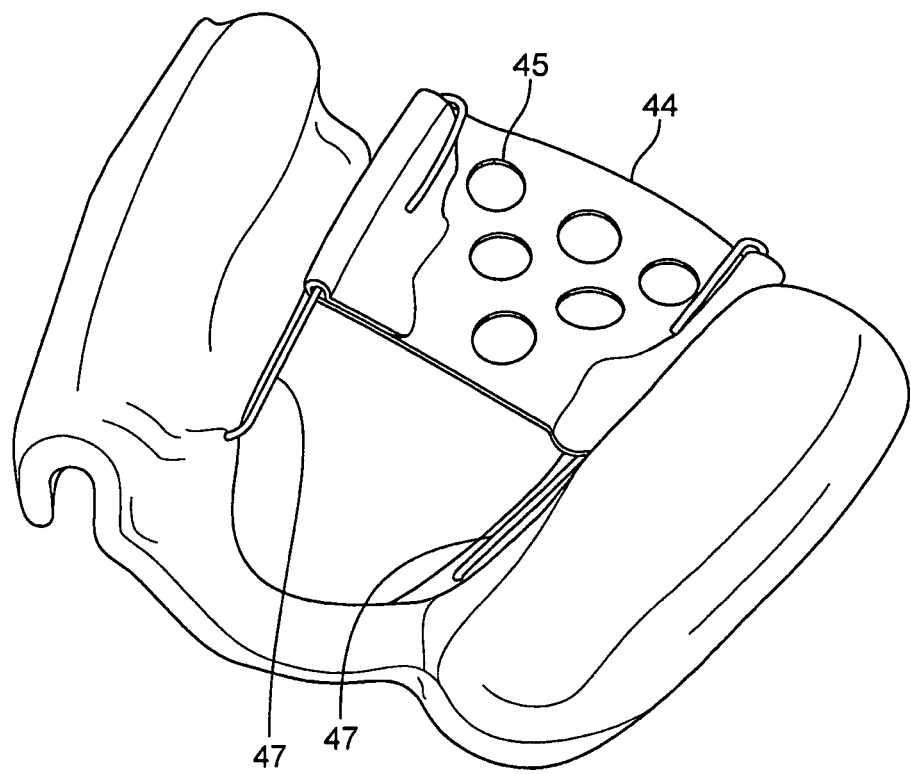

Referring to FIG. 5, in another embodiment, an oral appliance 40 includes a retaining band 44 formed of an elastic band or mesh that includes perforations 45 that in use contact the upper surface of the tongue and grip the tongue due to bulging of the tongue surface through the perforations 45. The elasticity of the band 44 allows the band to conform to the tongue while maintaining contact. The band 44 can have different shapes as shown in FIGS. 6 and 7, and, rather than being elastic, the band 44 can be formed of a rigid material and biased toward the surface of the tongue by a cantilevered wire 47 that exerts downward pressure on the tongue such that the tongue bulges through the perforations 45.

Figure 8:
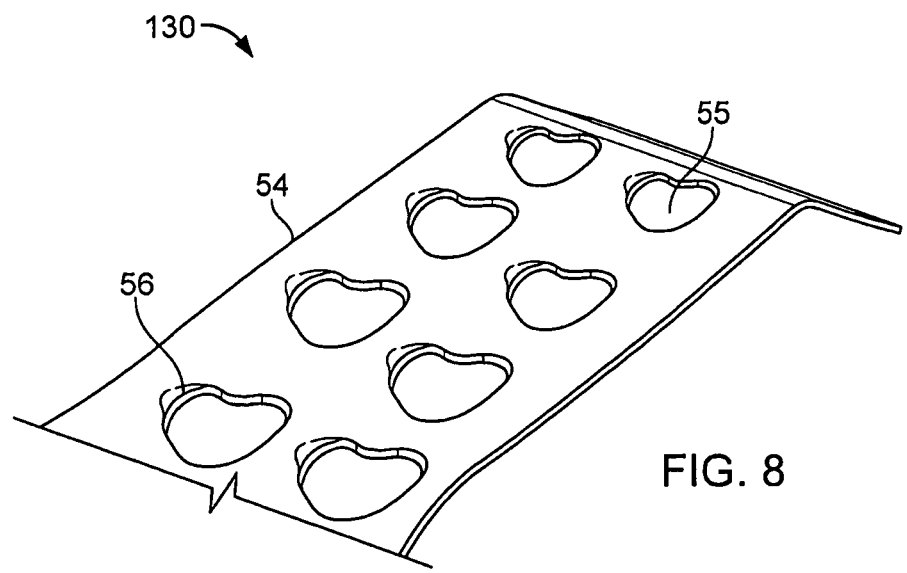
FIG. 8 illustrates a modified perforated retaining band.
Figure 9A:
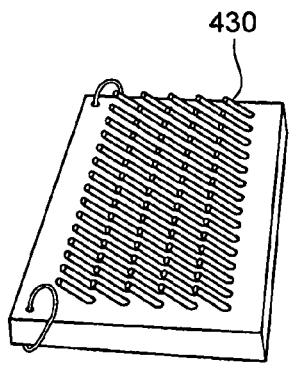
FIGS. 9a-11b show alternative retaining surfaces for contacting the user's tongue.
Figure 9B:
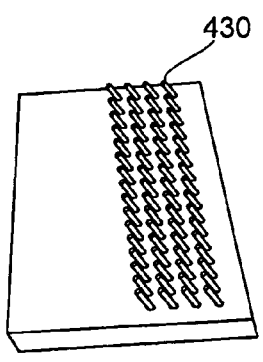
Figure 9C:
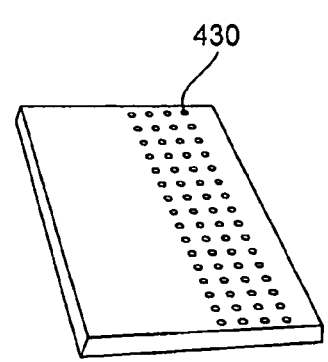
Figure 9D:
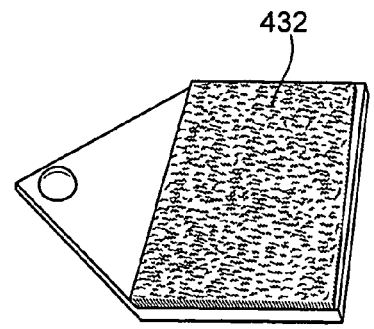
Figure 9E:
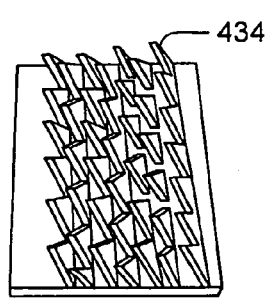
Figures 9F, 9G, 9H:
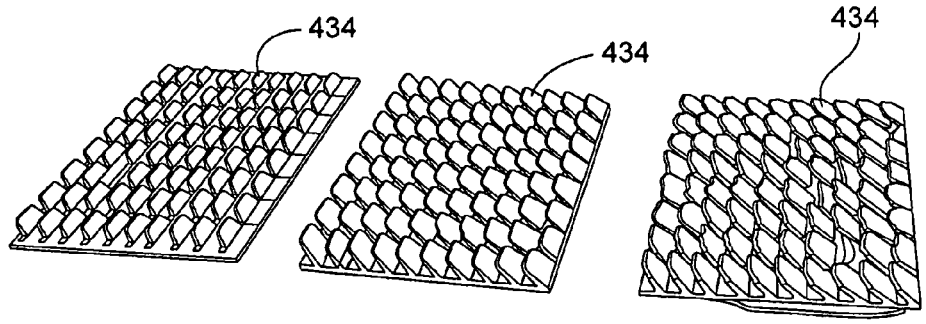
Figure 10A:
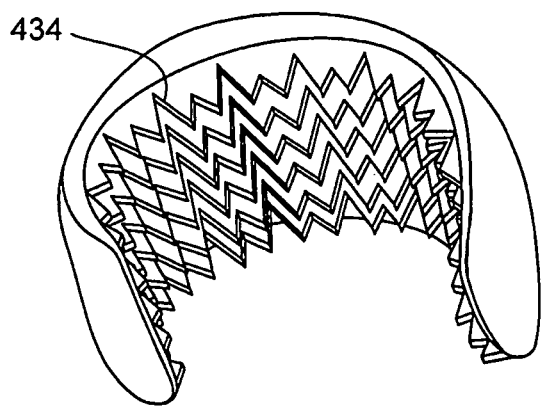
Figure 10B:
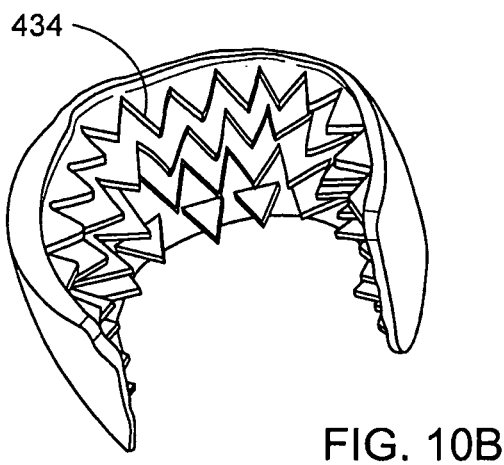
Figure 10C:
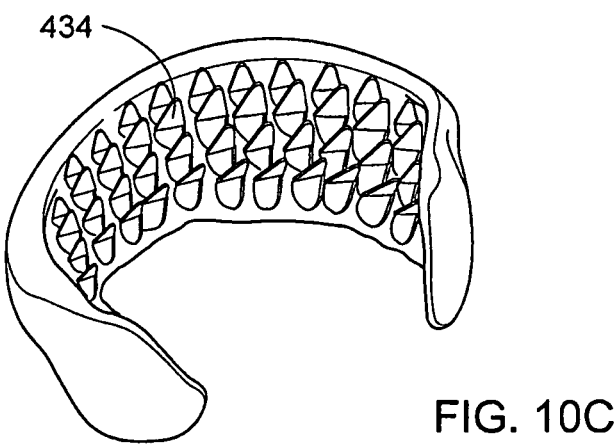
Figure 10D:
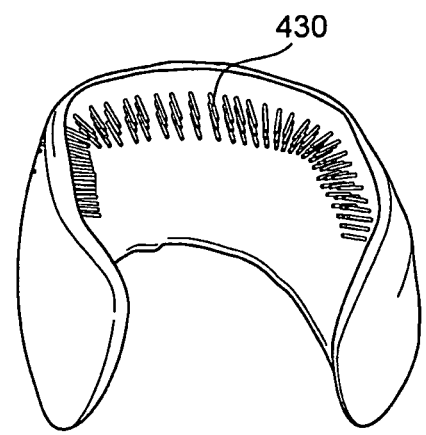
Figure 10E:
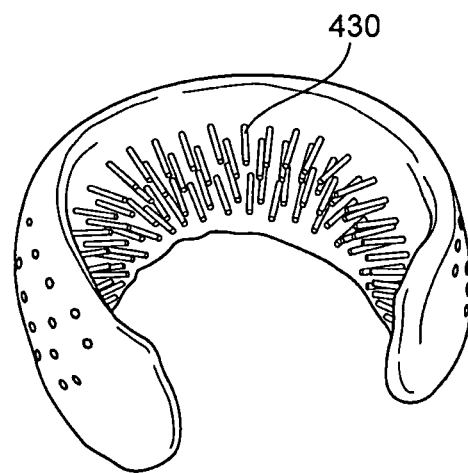
Figure 10F:
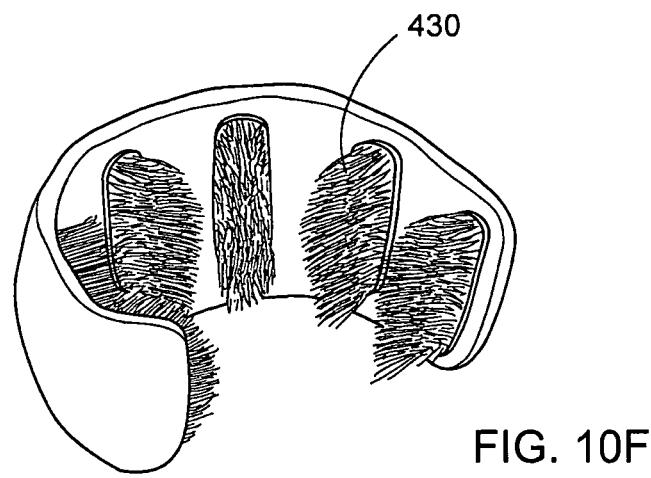

Rather than having circular perforations 45 in the retaining band, a retaining band 54, illustrated in FIG. 8, defines perforations 55 with a side 56 that protrudes like a cheese grater to help grip the surface of the tongue.

Figure 11A:
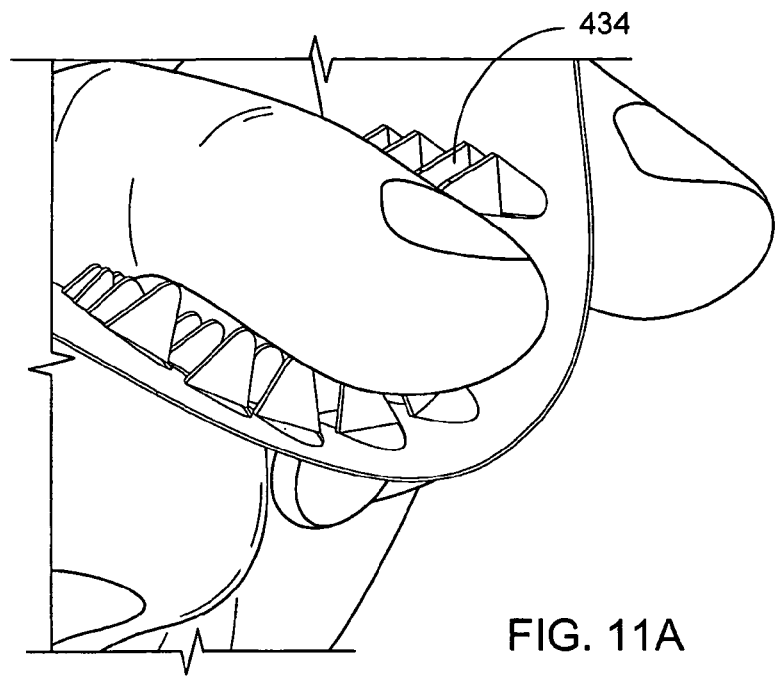
Figure 11B:
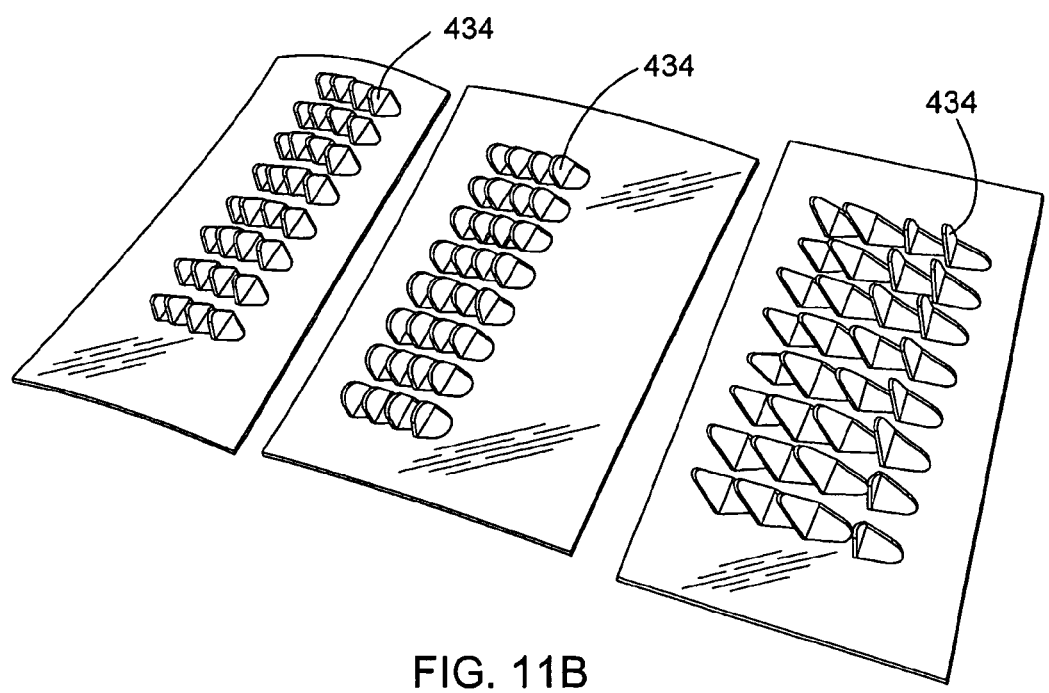

FIGS. 9-11 illustrate various retaining surfaces that can be employed on the tongue contacting side of the retaining band 34 in any of the embodiments described herein. In particular, FIGS. 9a-9c illustrate angled monofilament bristles 430 having diameters from about 0.14 to 0.35 mm; FIG. 9d illustrates a directional fur 432; FIG. 9e illustrates silicone triangular fins 434; FIGS. 9f-9h illustrate various alternative fins 434; FIGS. 10a-f illustrate various bristles 430, silicone fins, and polyester fins 434 that may be used as retaining texture; and FIGS. 11a and 11b illustrate patterns of polyester fins 434.

Figure 12A:
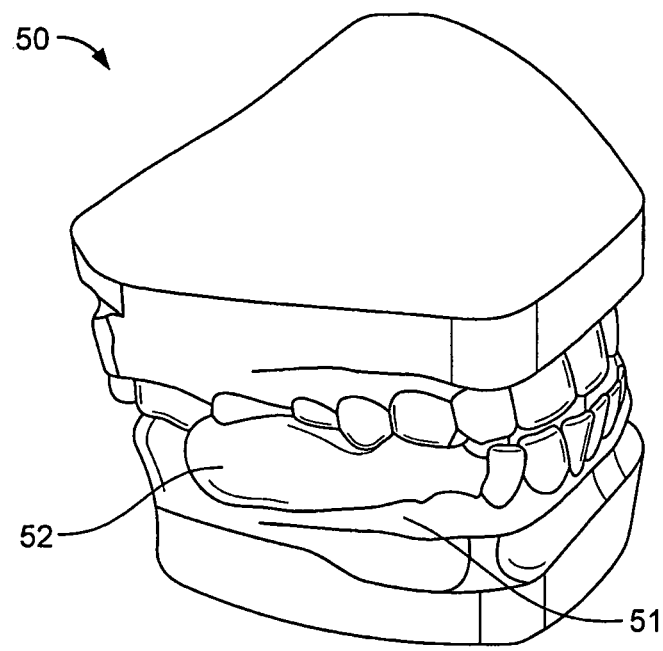
FIGS. 12a-13c illustrate tongue retaining oral appliances in which the retaining elements do not span completely across the width of the appliance.
Figure 12B:
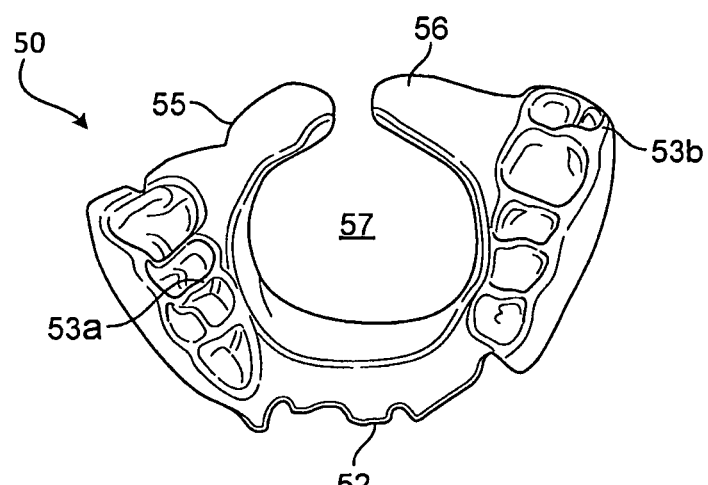

The oral appliance 50 of FIGS. 12a and 12b includes a frame 52 with mandibular attachments 53a, 53b for attaching the frame 52 to the bottom side teeth 51 of a user. Rather than having a retaining band that spans between the mandibular attachments, the frame 52 has two tongue contacting, retaining arms 55, 56, extending from the mandibular attachments 53a, 53b but not meeting. The frame 52 defines a central aperture 57 through which the user's tongue extends. In this embodiment, the mandibular attachments are molded to the upper and lower teeth of the user.

Figure 13A:
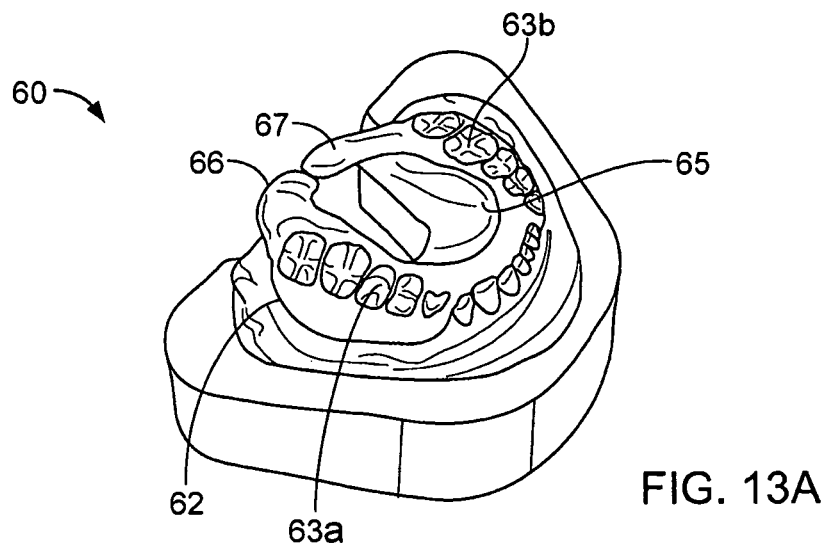
Figure 13B:
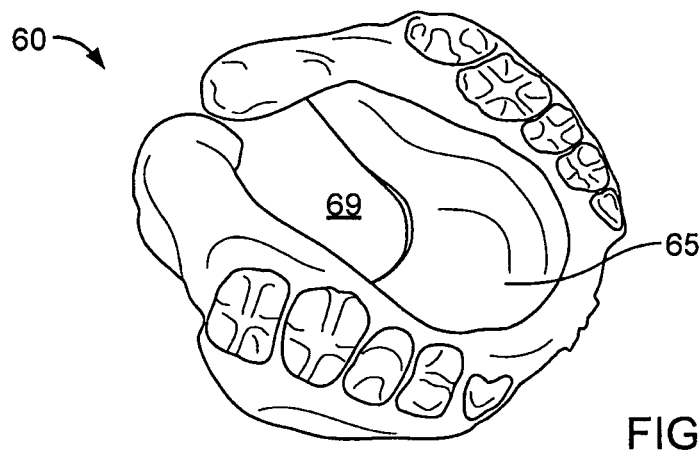
Figure 13C:
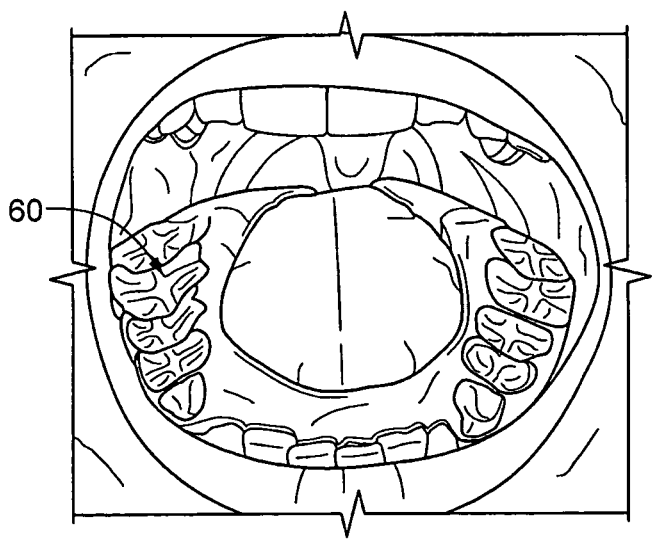

Referring also to FIGS. 13a-13c, a similar embodiment to that of FIG. 12 has retaining arms 66, 67 of a frame 62 of an appliance 60 extending from mandibular attachments 63a, 63b. The retaining arms 66, 67 of FIG. 13 are contoured downward and more closely follow the shape of the tongue than the flatter versions of the retaining arms 55, 56 of FIG. 12. Appliance 60 further includes a sloping region 65 extending from the front teeth region of the appliance 60 that helps guide the tongue through an aperture 69 of the frame 62.

Figure 14A:
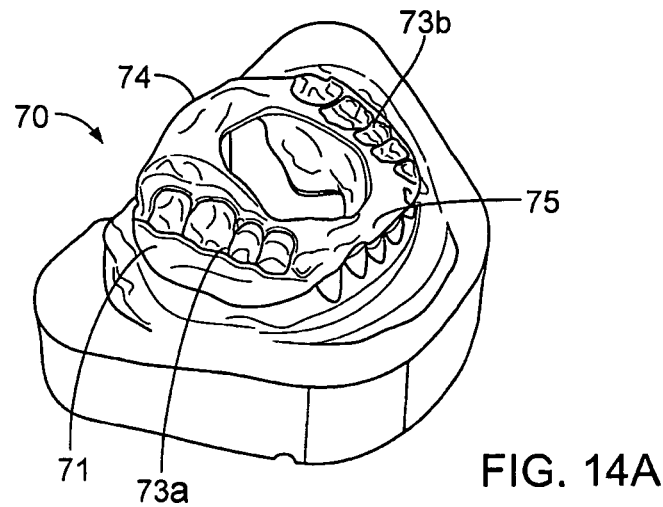
FIGS. 14a-14c illustrate a tongue retaining oral appliance that mounts to the lower teeth and is molded to the upper and lower teeth.
Figure 14B:
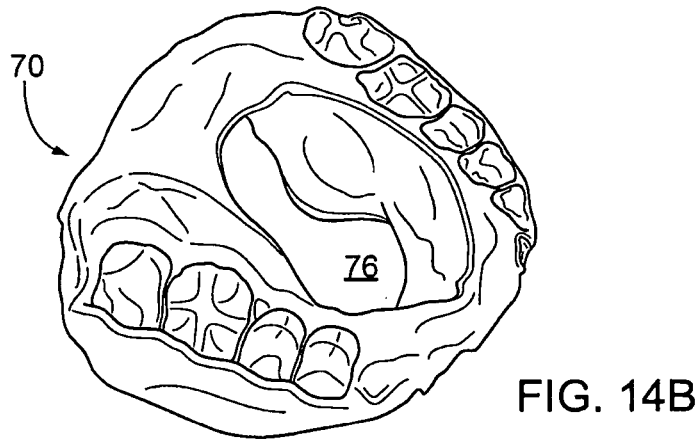
Figure 14C:
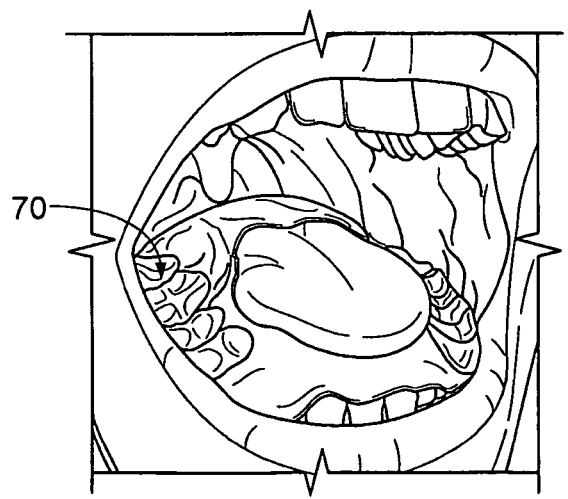

Referring to FIGS. 14a-14c, an oral appliance 70 that is similar to the embodiment of FIG. 3 includes a frame 72 with mandibular attachments 73a, 73b for attaching the frame 72 to the side teeth 71 of a user. The frame 72 has a tongue contacting, retaining band 74 that connects the mandibular attachments 73a, 73b and contacts the tongue in zone 82. Spanning between the mandibular attachments 23a, 23b along the inside of the front teeth is a bridge 75. The frame 72 defines a central aperture 76 through which the user's tongue extends. In contrast to the embodiment of FIG. 3, mandibular attachments 73a, 73b of appliance 70 are molded to the upper and lower teeth. The mandibular attachments 73a, 73b of appliance 70 also do not extend back into the mouth as far as the mandibular attachments of FIG. 3.

Figure 15A:
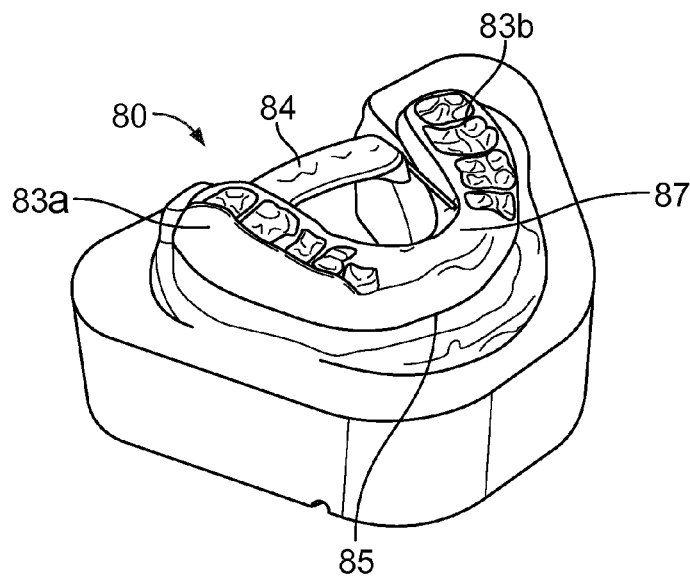
FIGS. 15a-15c illustrate a tongue retaining oral appliance having a retaining band that is cantilevered.
Figure 15B:
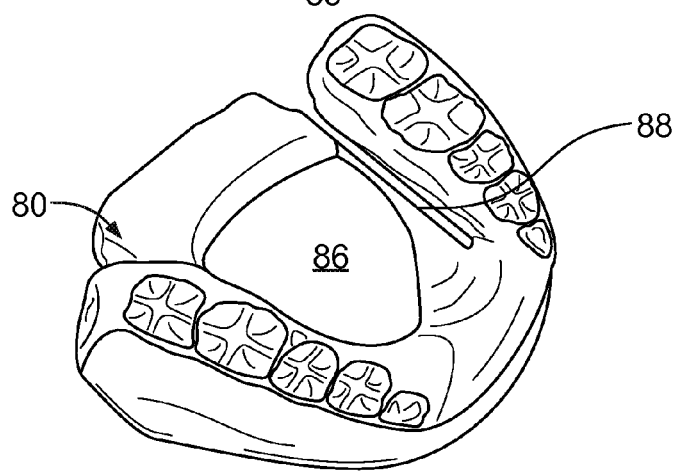
Figure 15C:
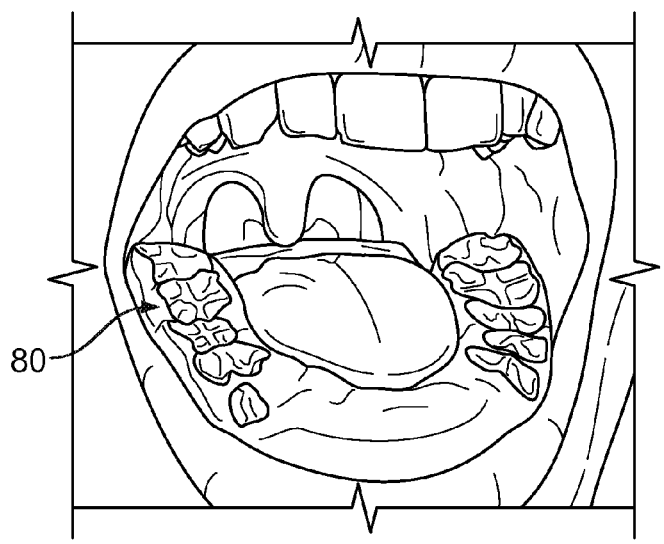

Rather than a retaining band spanning between mandibular attachments 83a, 83b, an oral appliance 80 of FIGS. 15a-15c includes a tongue contacting, retaining band 84 that is cantilevered off of a bridge 87 of a frame 85 of the appliance by wires 88. The bridge 87 connects the mandibular attachments 83a, 83b, running along and over the front teeth of the user. The frame 85 defines a central aperture 86 through which the user's tongue extends. In this embodiment, the mandibular attachments 83a, 83b are molded over the upper and lower teeth, and the bridge 87 is molded over the bottom teeth.

Figure 16A:
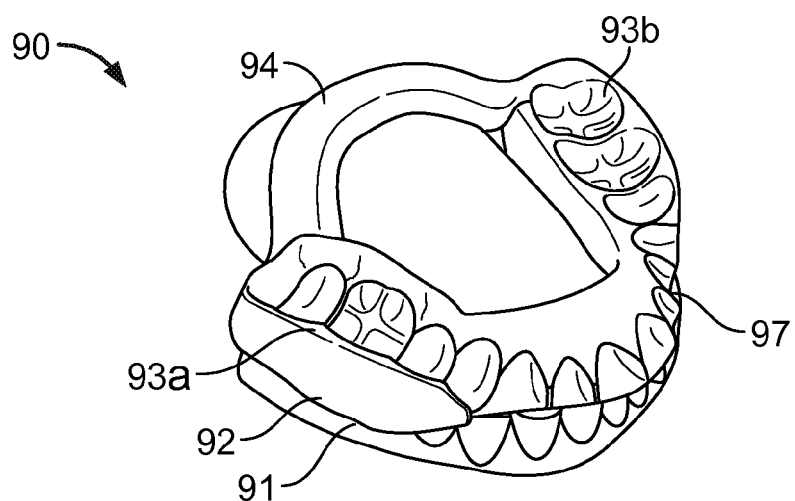
FIGS. 16a-16c illustrate alternative placements of the retaining band of a tongue retaining oral appliance.
Figure 16B:
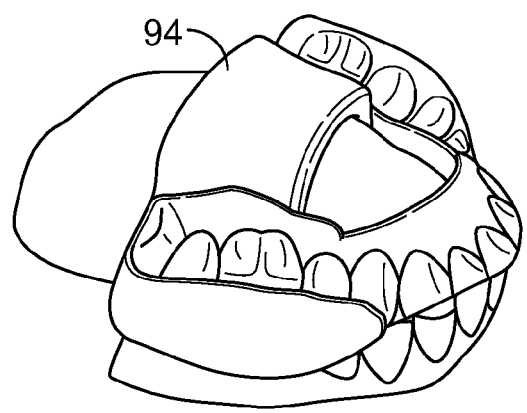
Figure 16C:
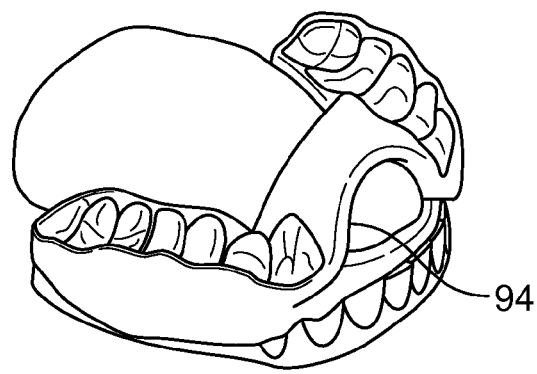

FIGS. 16a-16c illustrate alternative placements for the band 94 of an oral appliance 90 for users who find the placement more comfortable. The appliance 90 includes a frame 92 with mandibular attachments 93a, 93b for attaching the frame 92 to the side teeth 91 of a user. Spanning between the mandibular attachments 93a, 93b is a bridge 97 that in use is positioned between the upper and lower front teeth. Depending on user preference, the retaining band 94 can contact the tongue in zone 82 (FIG. 16a), further forward on the tongue but still in the molar region (FIG. 16b), or toward the tip of the tongue (FIG. 16c).

Figure 17:
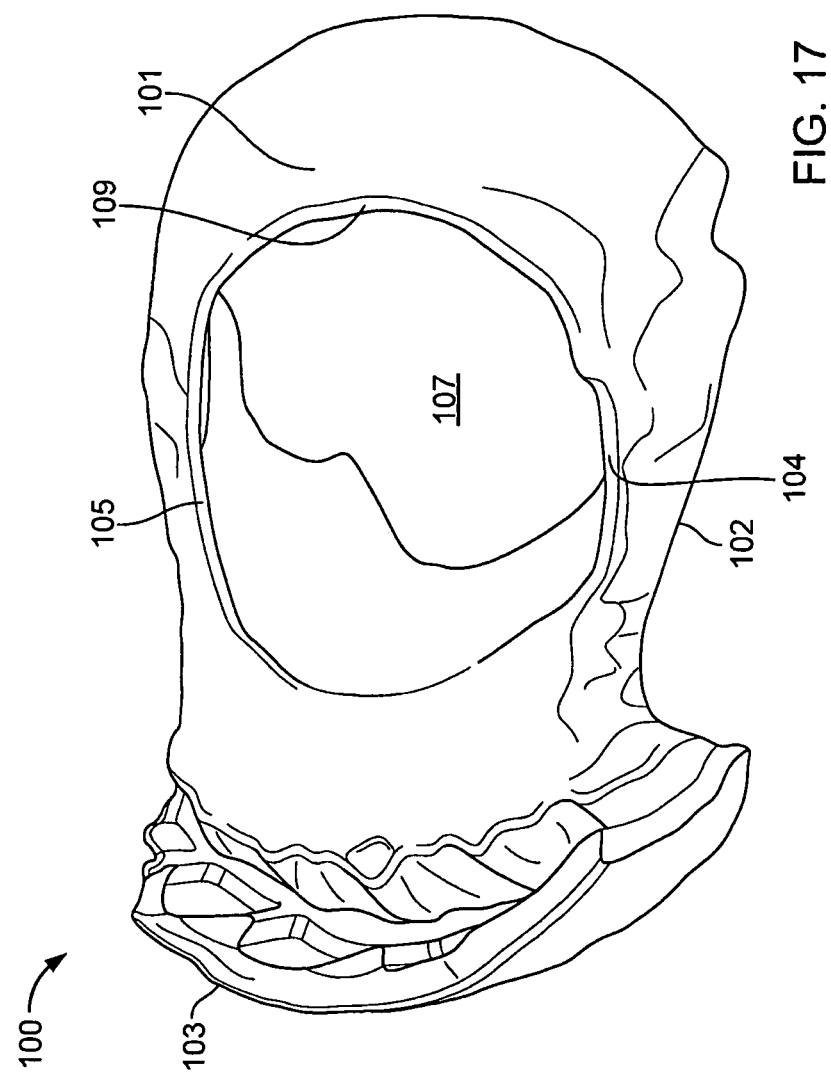
FIG. 17 illustrate a tongue retaining oral appliance that mounts to the bottom and top front teeth.

Referring to FIG. 17, an oral appliance 100 includes a frame 102 with a mandibular attachment 103 for attaching the frame 102 to the top and bottom front teeth of a user. The frame 102 has a tongue contacting, retaining band 101 with spaced, angled microfilament bristles (not shown) on a tongue contacting side 109 of the band 101, and extensions 104, 105 that connect the mandibular attachment 103 and the band 101. The frame 102 defines a central aperture 107 through which the user's tongue extends.

Figure 18A:
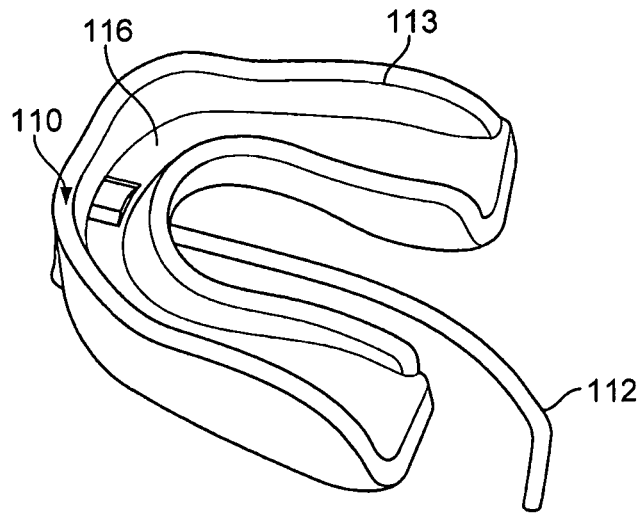
FIGS. 18a and 18b are top views of two alternative top teeth mounting tongue retaining oral appliances.
Figure 18B:
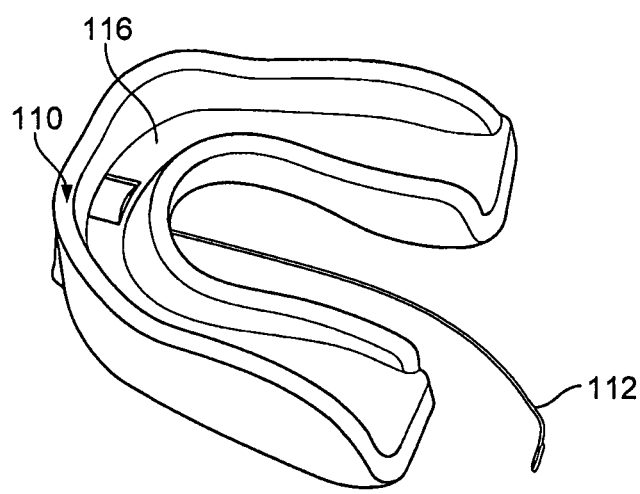

Referring to FIGS. 18a and 18b, an oral appliance 110 includes a mouth piece 113 for attaching the appliance 110 to the top teeth of a user. Extending rearward from a front teeth region 116 of the mouth piece 113 is a retaining element 112. The retaining element 112 is, for example, a wire or tube that extends backward and downward to contact the top surface of the user's tongue to limit backward movement of the tongue or to be suspended off of the surface of the user's tongue and limit backward movement of the tongue if it moves backward into contact with the retaining element. The retaining element 112 can include retaining surfaces as described herein.

Figure 18C:
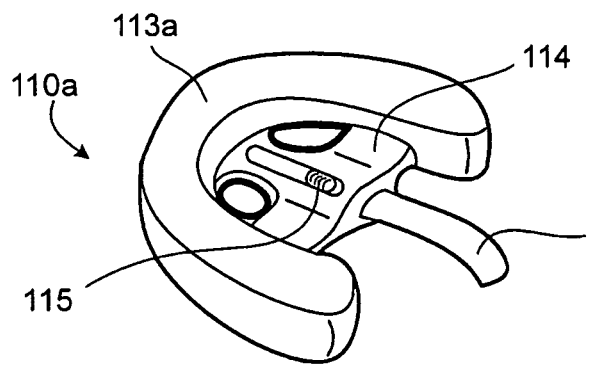
FIGS. 18c-18g illustrate tongue retaining oral appliances having retracting retaining elements.
Figure 18D:
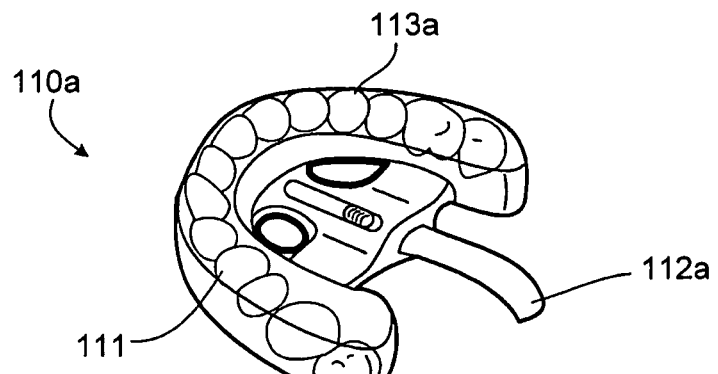
Figure 18E:
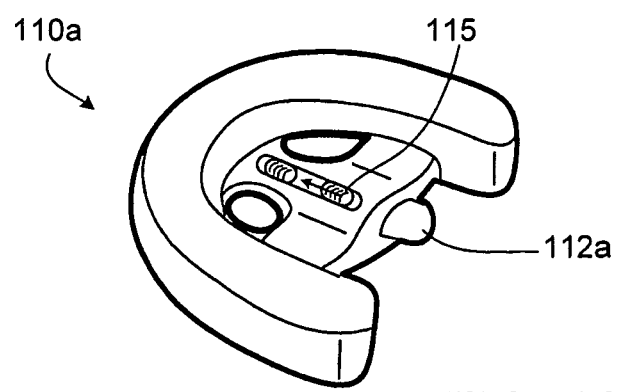

Another embodiment that attaches to the top teeth 111 is shown in FIGS. 18c-18e. In this embodiment, an oral appliance 110a has a mouth piece 113a with a roof member 114 from which a retaining element 112a extends. The retaining element 112a can be retracted into and extended from the roof member 114 using a lever 115. The figures show the lever 115 on the top side of the appliance 110a, which requires adjustment of the retaining element 112a prior to placement in the user's mouth. Alternatively, the lever 115 can be mounted to the bottom of the roof member 114 or can extend through the roof member 114 to the bottom of the roof member to provide access to the lever 115 after the appliance 110a has been placed in the user's mouth.

Figure 18F:
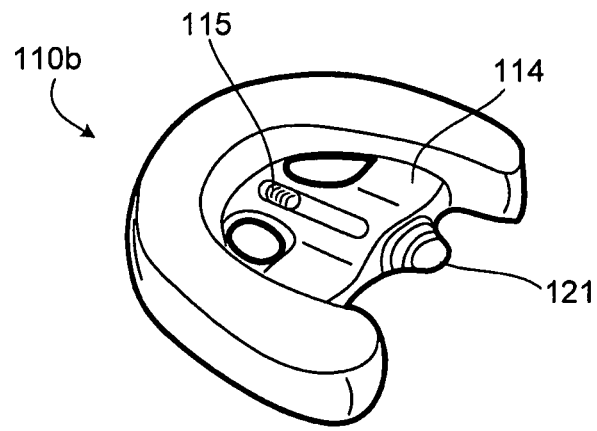
Figure 18G:
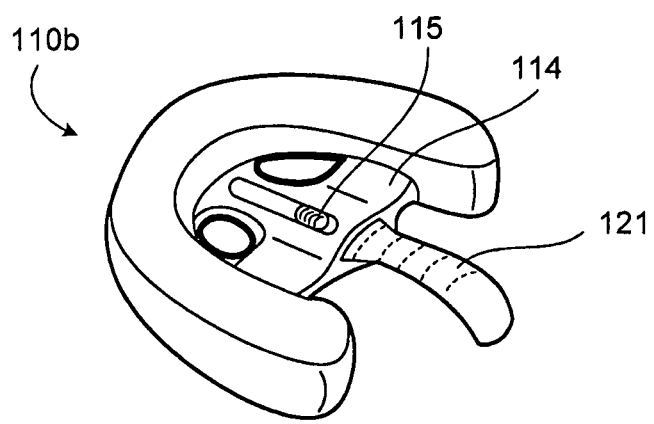

Alternatively, referring to FIGS. 18f and 18g, an oral appliance 110b includes a retaining element 121 formed of a collapsible sleeve that can be collapsed and extended using lever 115 without moving into and out of the roof member 114.

Figure 18H:
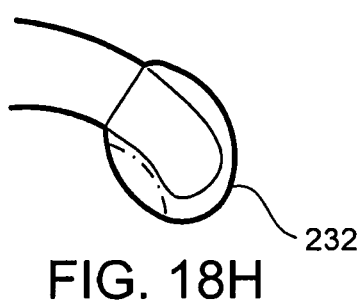
FIGS. 18h-18l illustrate alternative retaining element surfaces.
Figure 18I:
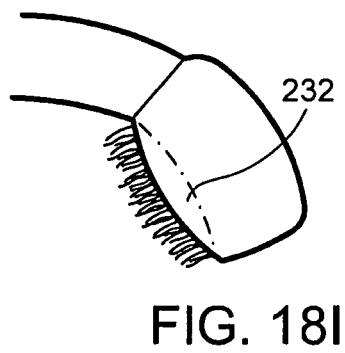
Figure 18J:
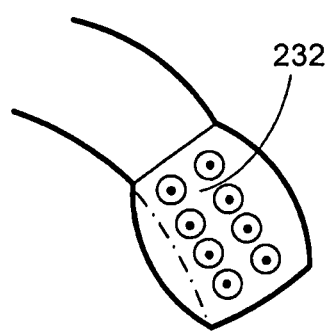
Figure 18K:
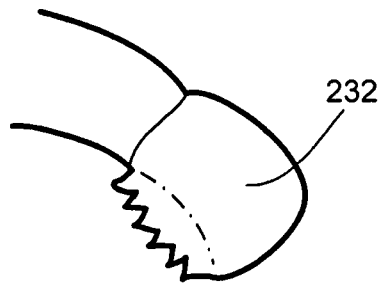
Figure 18L:
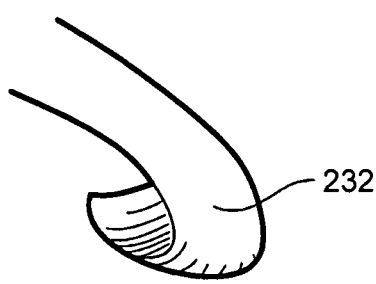
Figure 19A:
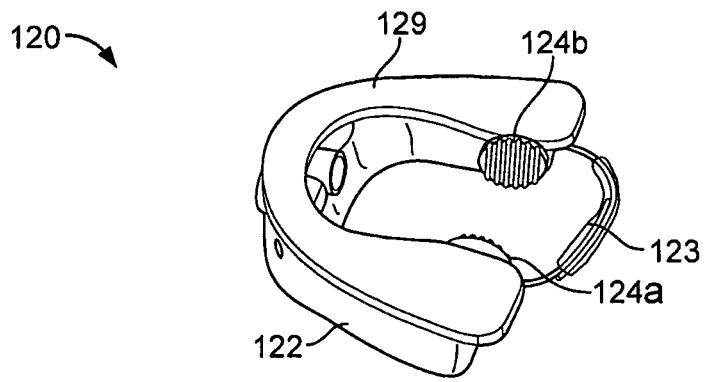
FIGS. 19a-20c illustrate tongue retaining oral appliances including grippers for contacting the sides of the user's tongue.
Figure 19B:
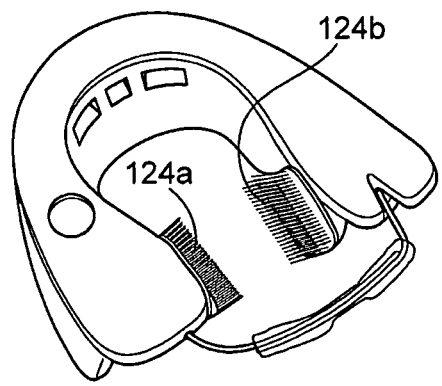
Figure 19C:
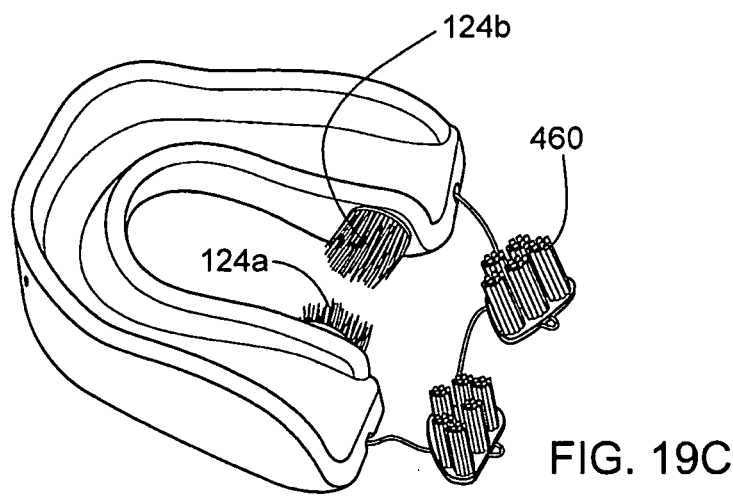

The retaining surface of the retaining element 232 can have, for example, an atraumatic silicone cover that can be sticky (FIG. 18h), bristles (FIG. 18i), suction cups (FIG. 18j), angled fins, ridges or cones (FIG. 18k), and/or a spring hook (FIG. 18l). FIG. 18h shows an atraumatic silicone cover that contacts the tongue. It could be sticky, small ridges or cones that contact the tongue Referring to FIG. 19a, an oral appliance 120 includes a frame 129 with a retainer 122 for attaching the frame 129 to the top row of teeth of a user. The frame 129 has a tongue contacting, retaining band 123 that connects to the retainer 122. The retaining band 123 can include microfilament bristles 460 (FIG. 19C) and the retaining band can be made of wire. On either side of the retainer 122 close to where the band 123 connects to the retainer 122, the frame 129 includes contacting members 124a, 124b. The contacting members 124a, 124b help to hold the tongue in place during use. Alternative contacting members 124a, 124b are shown in FIGS. 19b and 19c.

Figure 20A:
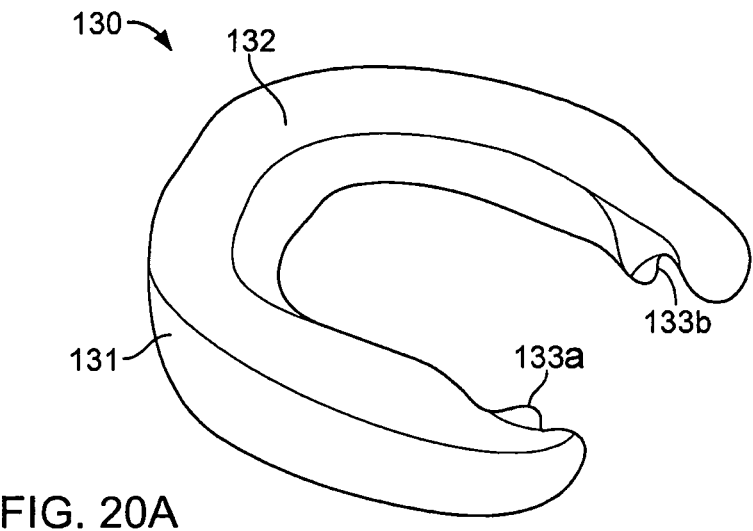
Figure 20B:
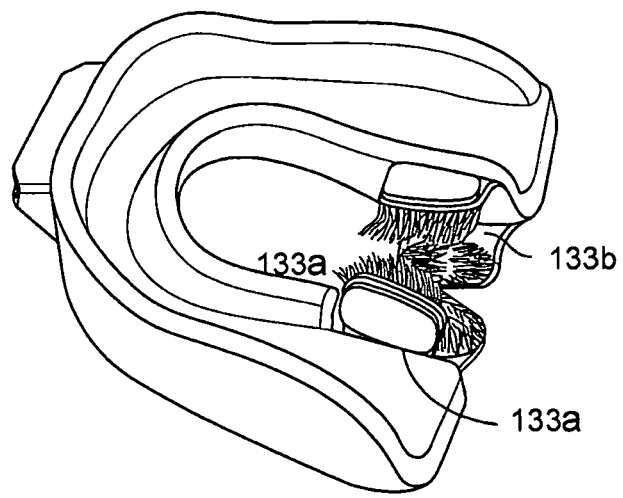
Figure 20C:
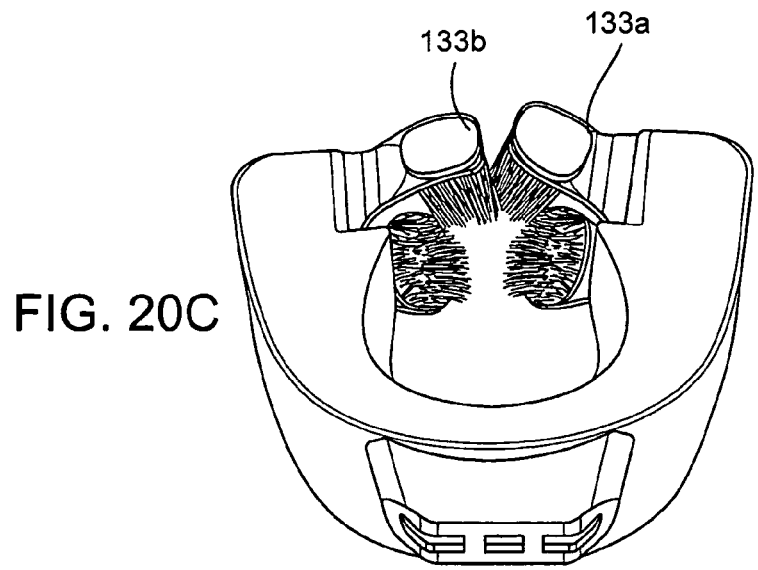

Referring to FIGS. 20a-20c, according to another embodiment, an oral appliance 130 includes a frame 131 with a retainer 132 for attaching the frame 131 to the bottom row of teeth of a user. Alternatively, this embodiment can be mounted to the top teeth. The frame 131 has pinch members 133a, 133b at the ends of the sides of the retainer 132. The pinch members 133a, 133b can include microfilament bristles that in use lightly grab onto the sides of the user's tongue to limit backward movement of the tongue.

Figure 21A:
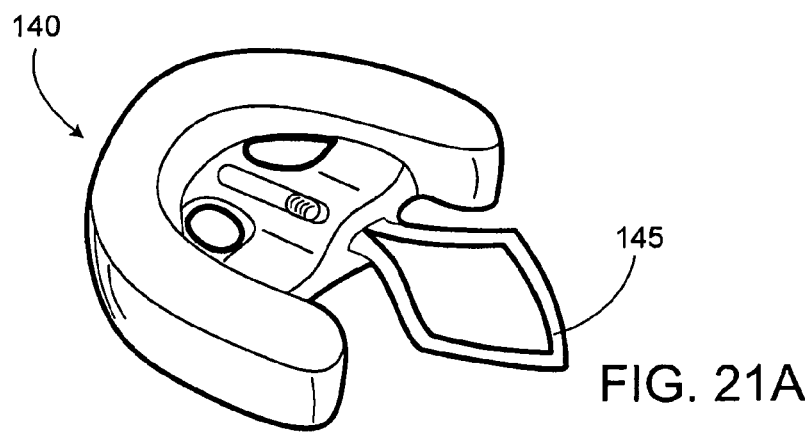
FIGS. 21a and 21b illustrate another tongue retaining oral appliance having a retracting retaining element.
Figure 21B:
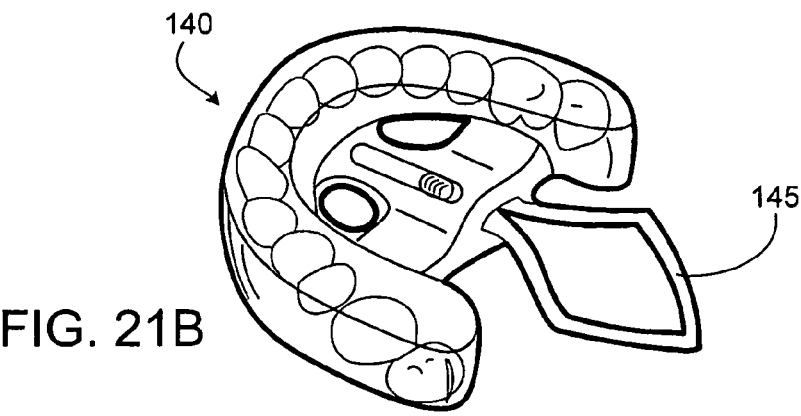

The oral appliance 140 of FIGS. 21a-21c is similar to that of FIG. 18c but in this embodiment includes a diamond shaped wire retaining element 145 for contacting a larger surface area of the tongue.

Figure 22A:
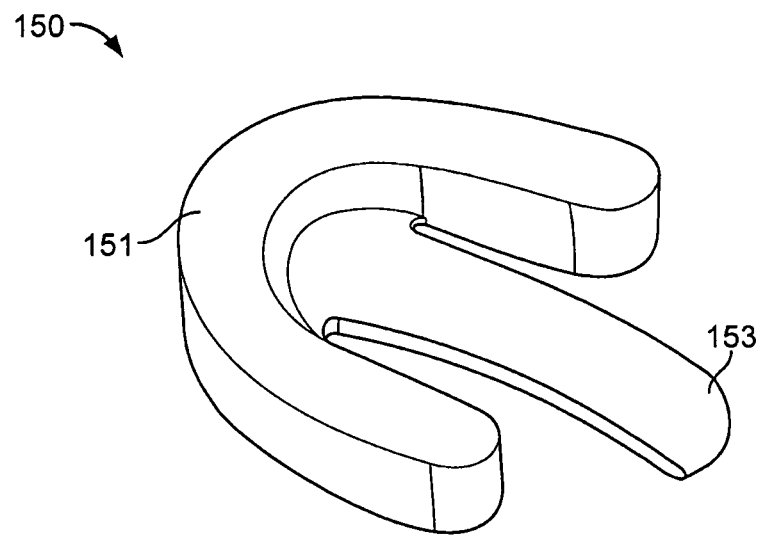
FIGS. 22a and 22b illustrate additional upper teeth mounted tongue retaining oral appliances.
Figure 22B:
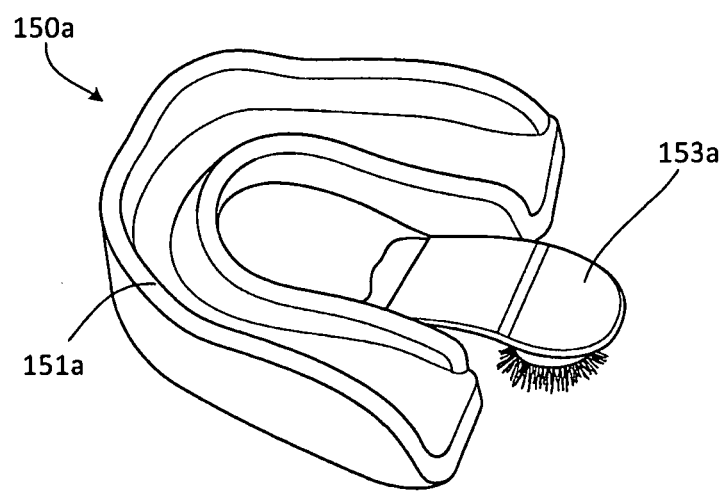

Referring to FIG. 22a, rather than having a retracting retaining element, an oral appliance 150 that mounts to the user's top teeth includes a fixed retaining element 153. The retaining element 153 extends from a frame 151 of the appliance and curves downward to engage the top of the user's tongue. The oral appliance 150a of FIG. 22b has the retaining element 153a mounted to the sides of the frame 151a rather than the front teeth region.

Figure 23A:
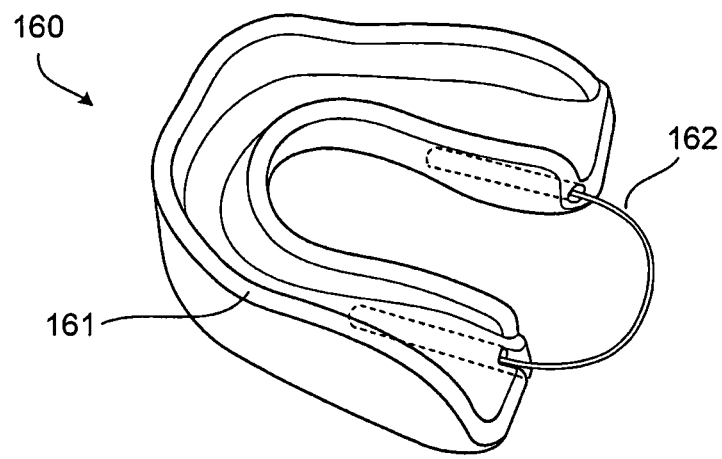
FIG. 23a illustrates a tongue retaining oral appliance with a wire-loop, retractable retaining element.
Figure 23B:
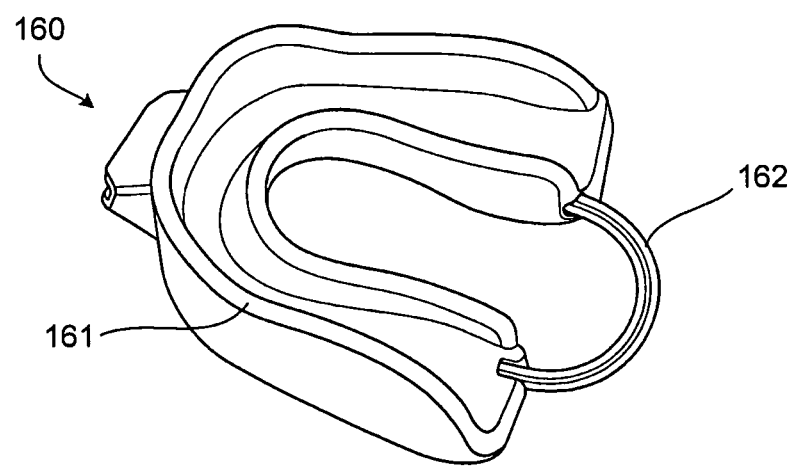
FIGS. 23b and 23c show the wire-loop retaining element in a retracted state and an extended state, respectively.
Figure 23C:
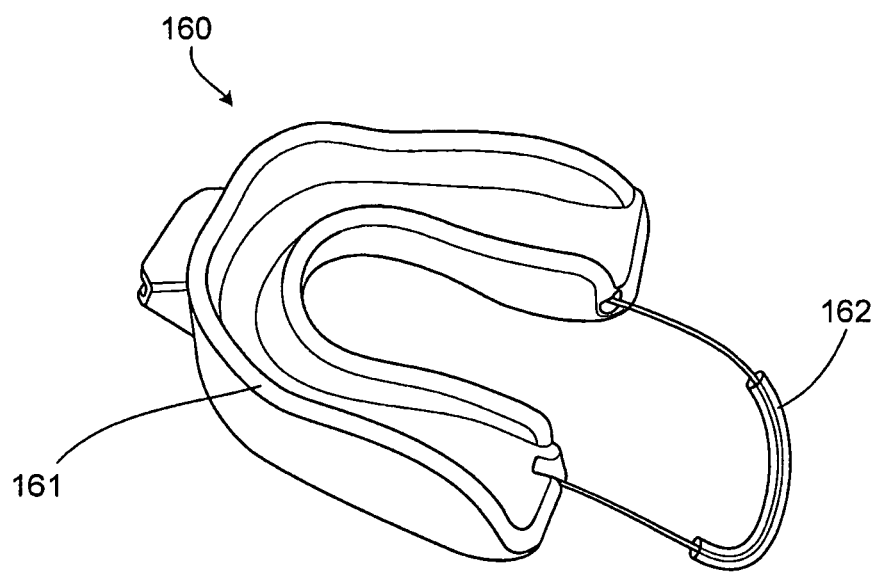

The oral appliance 160 of FIG. 23a mounts to the top teeth and includes a frame 161 with a retractable retainer element 162. The retaining element 162 is shown in the retracted position in FIG. 23b and the extended position in FIG. 23c.

Figure 24A:
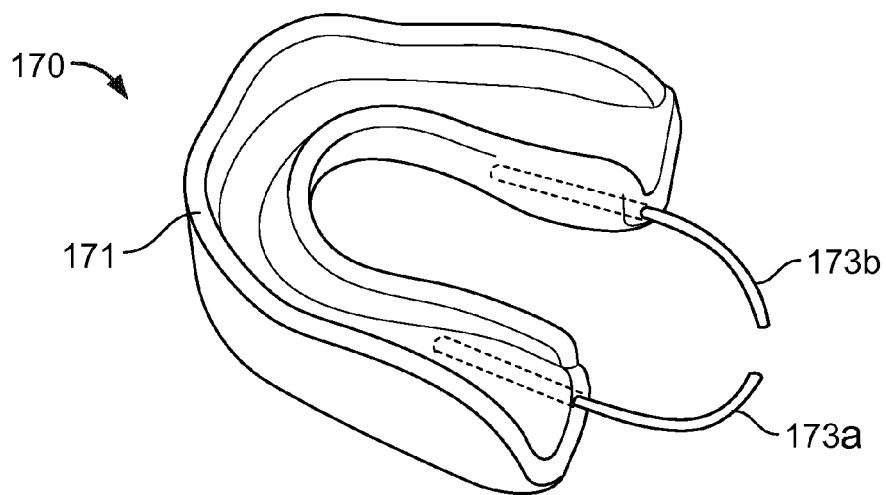
FIGS. 24a-24c illustrate additional retracting retaining elements.
Figure 24B:
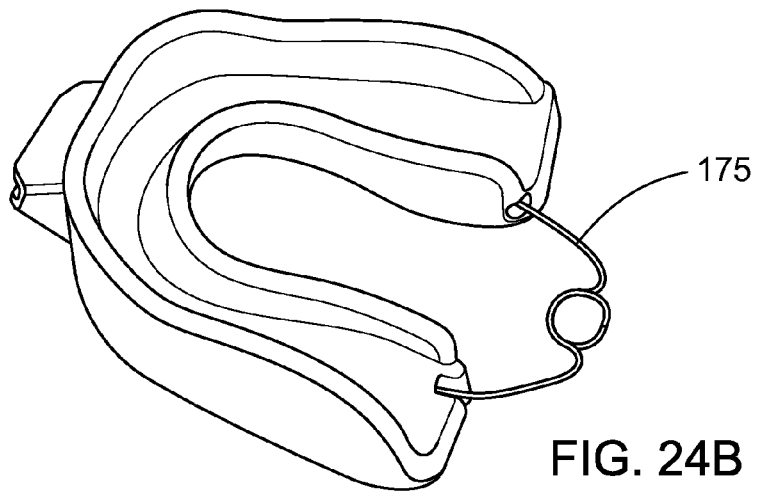
Figure 24C:
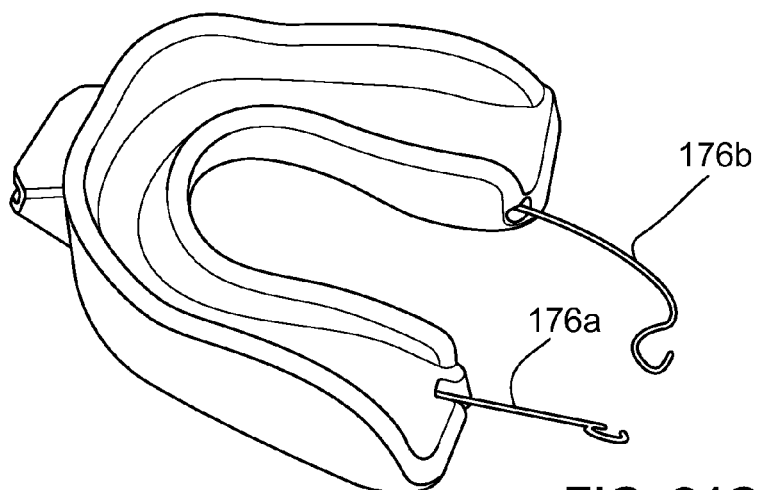

FIGS. 24a-24c illustrate additional configurations of retaining elements. The oral appliance 170 of FIG. 24a includes a frame 171 that mounts to the top teeth of the user. The frame 171 includes two retaining arms 173a, 173b that can be retracted and extended using levers. The retaining element 175 of FIG. 24b has a coiled region to increase the surface area of contact with the tongue. The retaining element 175 is formed by two retaining arms 176a, 176b (FIG. 24c) having hooked ends. FIG. 24c shows an interim position of deployment of the final deployed position shown in 24b. The arms 176a, 176b are stored unextended with the loops vertical. The arms 176a, 176b are deployed backward and then rotated from the position shown in FIG. 24c to that of FIG. 24b.

Figure 25A:
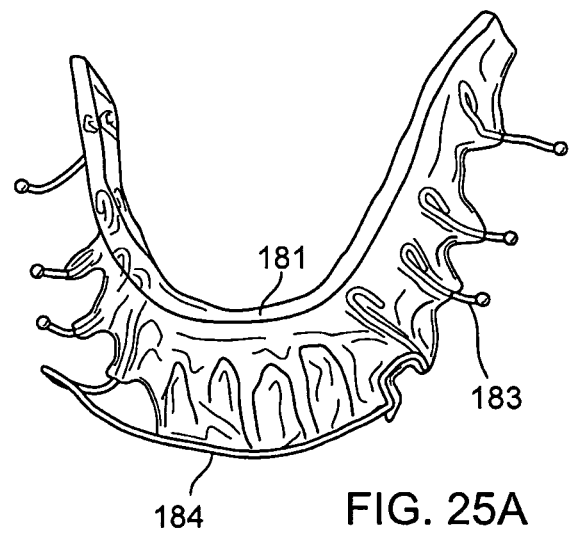
FIGS. 25a and 25b illustrate orthodontic retainers.
Figure 25B:
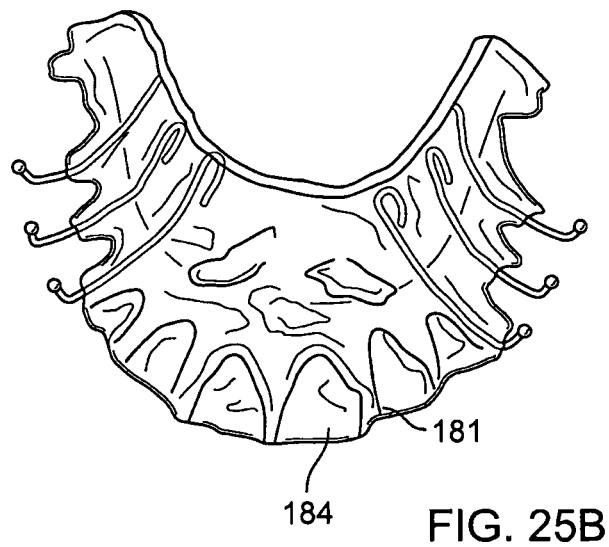

Referring to FIGS. 25a and 25b, according to another embodiment, a standard orthodontic retainer 184 for the upper or lower teeth that includes a frame 181 with wire elements 183 for attaching the frame 181 to the user's teeth can be modified to include a retaining band as described herein.

To enhance user comfort, it can be advantageous to minimize the amount of material placed in the user's mouth to permit the tongue to sit in its normal awake position, minimize saliva production, and limit interference with the user's normal jaw and teeth position. Furthermore, minimizing the amount of material placed in the user's mouth allows the user's jaw to sit at the correct angle and does not force front of jaw down.

Figure 26A:
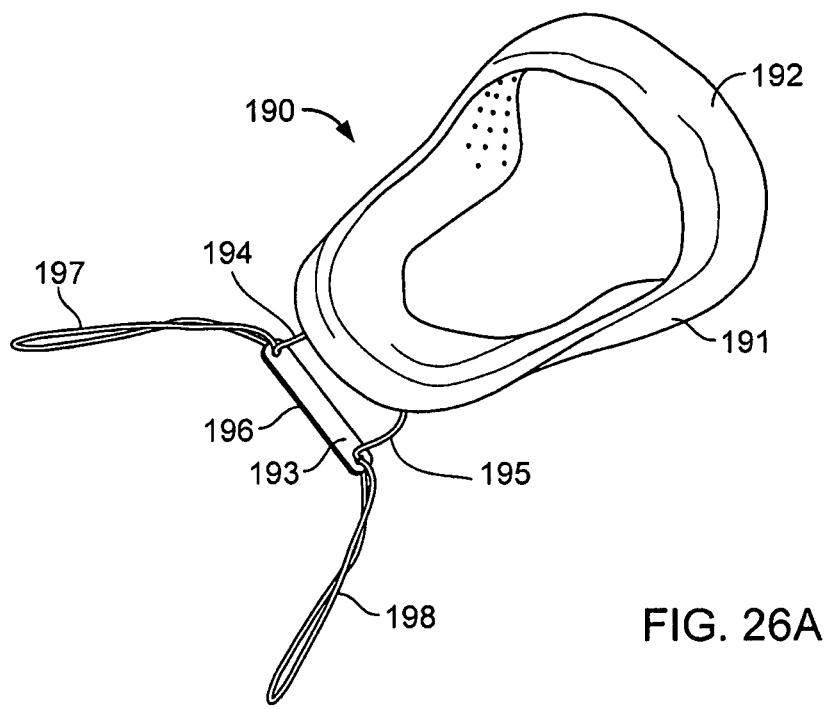
FIG. 26a is a top view of another tongue retaining oral appliance having a threaded mounting element.
Figure 26B:
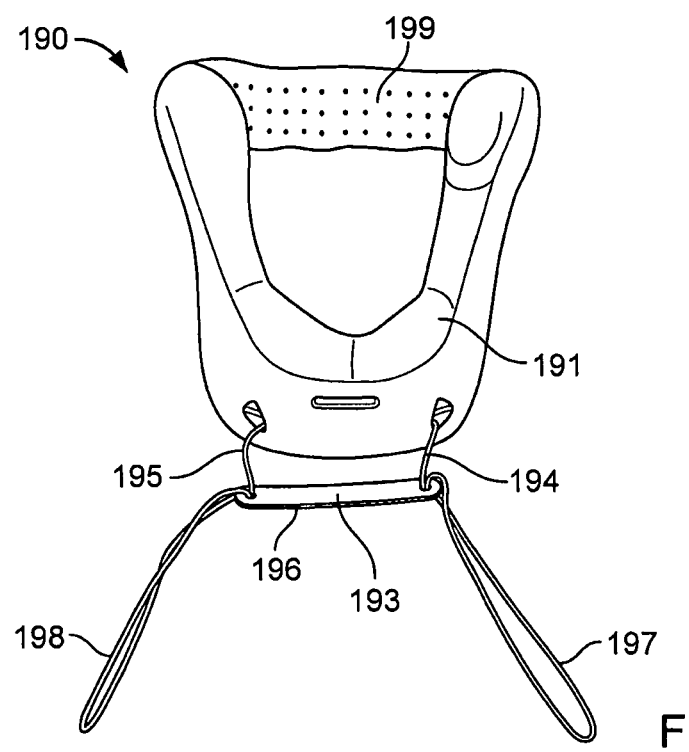
Figure 26C:
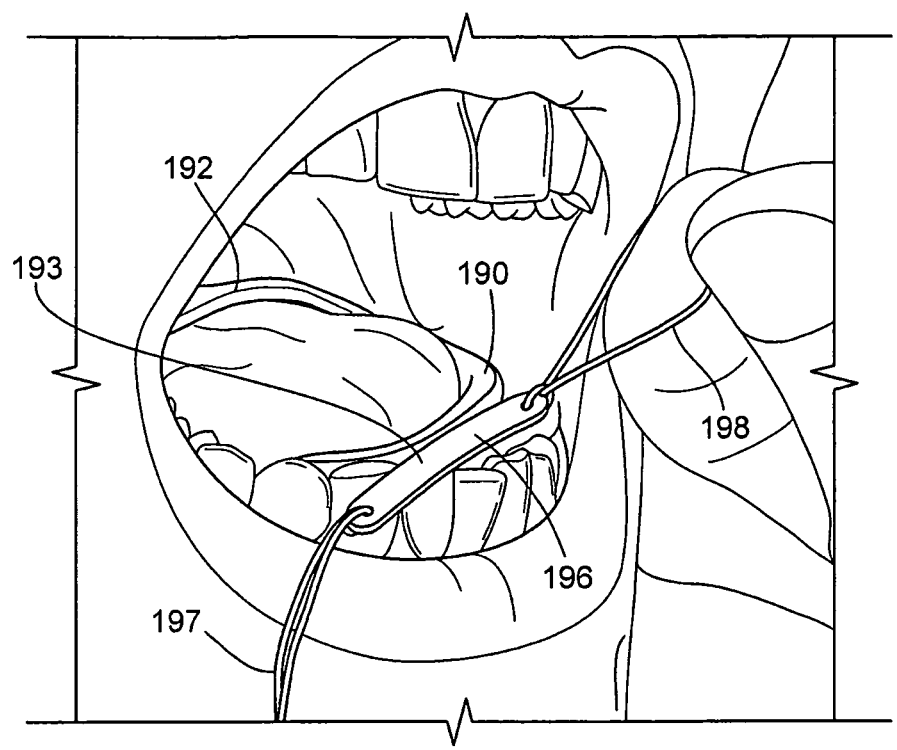
FIG. 26c illustrate the tongue retaining oral appliance of FIG. 26a being removed from a user's mouth.

Referring to FIGS. 26a-26c, in an embodiment that does not include any features that cover the bite contacting surfaces of the teeth, an oral appliance 190 includes a frame 191 with a retaining band 192, and a floss mount 193. The floss mount 193 includes two thread connectors 194, 195 to attach the frame 191 to the user's bottom front teeth. Between the thread connectors 194, 195 is an elastic band 196 that when positioned in the user's mouth stretches to tension the appliance 190 to the teeth. The appliance 190 also includes two grab loops 197, 198 that can be used to position the thread connectors 194, 195 between the teeth and to remove the thread connectors 194, 195 from between the teeth. The retaining band 192 can be textured with one-way bristles or silicone fins, as described above, or with any of the other described retaining surfaces, on a tongue contacting side 199 of the band 192. In use, the retaining band 192 wraps around the top of the user's tongue between the wisdom teeth.

Rather than two thread connectors, the oral appliance 190 can include a single thread connector that extends from the center of the front section of the frame 191 and in use is placed between the user's lower middle teeth, as describe below. As an alternative to thread connectors, an adhesive material, such as used in Crest® Whitestrips, such as the Crest 3D White Whitestrips Professional Effects, can be placed on the teeth contacting side of the frame 191 to attach the oral appliance 190 to the back of the user's lower teeth.

Alternatively, the anchoring can be a flexible strip along the side of the device that attaches to the inside surface of the teeth on the lower jaw. The attachment can be a flexible adhesive strip that goes up over the front of the teeth. It can have adhesive only on the part that contacts the front of the teeth or it can be on the part that contacts the front and back of the front teeth or just can be adhesive on back of front teeth. The adhesive can be one such as on the newest generation of Crest® Whitestrips.

The oral appliance 200 of FIGS. 27a-27d also has features that fit within the lingual surfaces of the teeth with an attachment below the bite contacting surfaces of the lower teeth. To secure the oral appliance 200 in the user's mouth, the oral appliance 200 includes a floss mount 202 that extends between the user's lower middle teeth and anchors between the lower teeth and the inside surface of the user's lower lip.

The oral appliance 200 is in the form of a tongue engagement element 204 having a front region 206, a rear band region 208, and side regions 210, 212. The front, rear and side regions form a loop defining an opening 214 for receiving a user's tongue. The side regions 210, 212 extend back and outward from the front region 206 to the rear region 208 such that the rear region 208 is wider than the front region 206. The front region 206 has an upper surface 216 and the rear region 208 has a lower surface 218. The rear region 208 extends upward relative to the front region with respect to a user's mouth such that the lower surface 218 is spaced from the upper surface 216 to receive the user's tongue therebetween. The rear region 208 includes structures 220, for example, tongue engaging filaments, which extend inward from the lower surface 218 to engage the top of the user's tongue and from inner surfaces 222, 224 of the rear region 208 to engage the sides of the user's tongue. In a preferred embodiment, the diameter of the structures 220 are sized to fit within the papillae. Furthermore, in a preferred embodiment, the structures 220 have sufficient stiffness to resist prolapsing when subjected to a force by the weight of the tongue when the user is supine.

Referring to FIGS. 28a-28d, the tongue engagement element 204 is shaped such that when placed in a user's mouth and without interfering with the user's normal bite, the element 204 wraps around the tongue 404 with the rear region 208 extending over the user's tongue to rest on the tongue, the side regions 210, 212 extending along the floor of the user's mouth cavity under the tongue, and the front region 206 extending under the user's tongue. The rear region 208 is generally arch shaped with piers 226, 228 (FIG. 27a) such that the rear region 208 curves over the tongue. The piers 226, 228 include the inner surfaces 222, 224, respectively, that include the structures 220 for engaging the sides of the user's tongue The tongue engagement element 204 can be provided in different sizes to accommodate different sized mouths. For example, referring particularly to FIGS. 27b and 27d, the height, H1, can be range from about 19 to 24 mm, and the width, W1, can range from about 30 to 37 mm, depending on the size of the user's mouth, as discussed further below. The tongue engagement element 204 has a length, L1, for example, of 41.7 cm, which is greater than the width, W1. While the length, L1, may vary depending on the size of the user's mouth, the length, L1, will generally be greater than the width, W1. The length, L2, of the side regions 210, 212, is, for example, 21.7 mm. The overall width, W2, and height, H2, of the tongue engagement element is, for example, in the range of 35 to 42 mm, and 24 to 29 mm, respectively, and the spacing, H3, between surfaces 216 and 218 is, for example, in the range of 13 to 18 mm. The structures 220 have a length of, for example, 4 mm, and a diameter of, for example, 0.3 mm. The rear region 208 is, for example, 7.5 mm wide and from 2.5 to 4.5 mm thick. In a particular embodiment, the body of the appliance is made from a material with a durometer of 87 shore A, which gives the right balance of stiffness and elasticity. The tongue engagement element 204 can be made to be adjustable, as in embodiments described above, such that the length, L1, and the height, H3, can be determined by the user.

The floss mount 202 (FIG. 27a) that secures the oral appliance 200 in the user's mouth includes an anchor 230 and two members 232, 234, for example, dental floss, connecting the anchor (attachment handle) 230 to the tongue engagement element 204. In use, floss member (attachment string) 232 is positioned between the user's two front lower teeth #24 and #25 (FIG. 28b) and floss member 234 is positioned over the user's front teeth. Floss member 234 acts as a safety to prevent the anchor 230 from becoming detached from the oral appliance 200 if the floss member 232 becomes damaged.

Figure 28D:
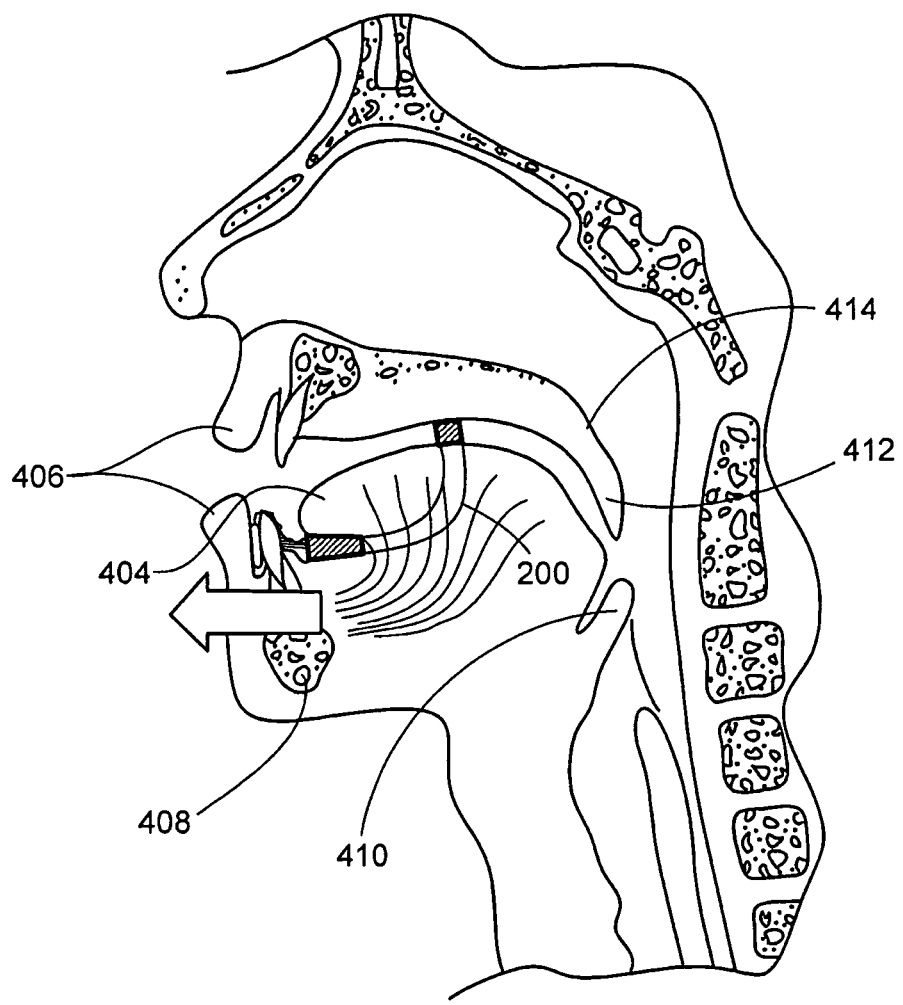
Figure 29A:
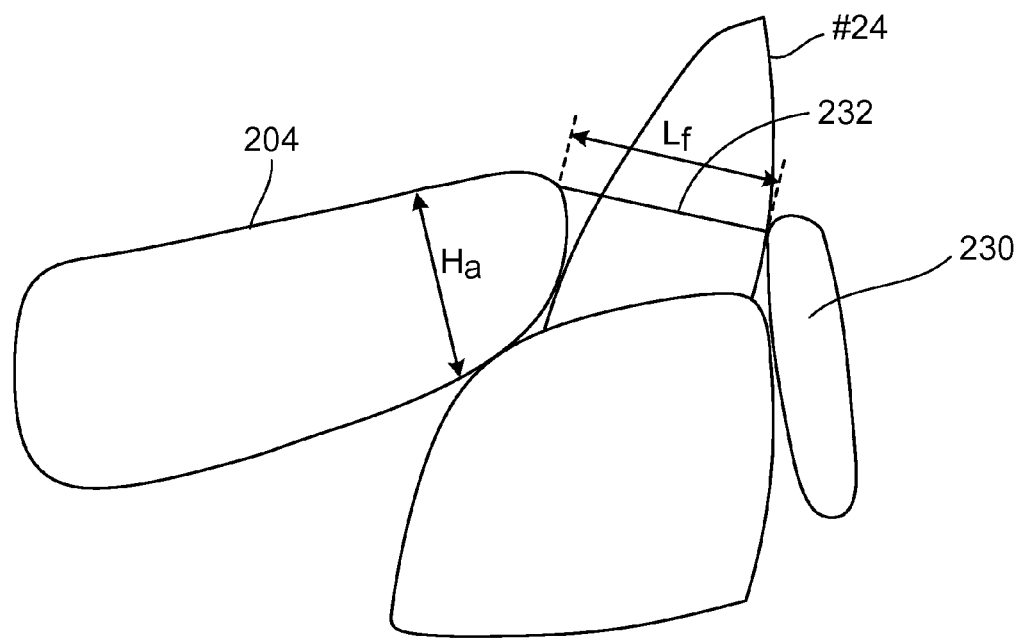

With the oral appliance 200 positioned in the mouth and the floss member 232 between the front lower teeth, the anchor 230 resides between the user's teeth and the user's lower lip 406, lying flat against the teeth. The mandible 408, epiglottis 410, uvula 412, and soft palate 414 are also shown in FIG. 28D for reference. Referring to FIG. 29a, the length, Lf, of the floss member 232, for example, 4.5 mm, and the height, Ha, of the floss member 232's point of connection on the tongue engagement element 204, for example, 5 mm, relative to the thickness of the lower front teeth are preferably sized such that the floss member 232 is spaced from the gum, limiting the floss member 232 from resting on the gum and causing irritation.

Figure 29B:
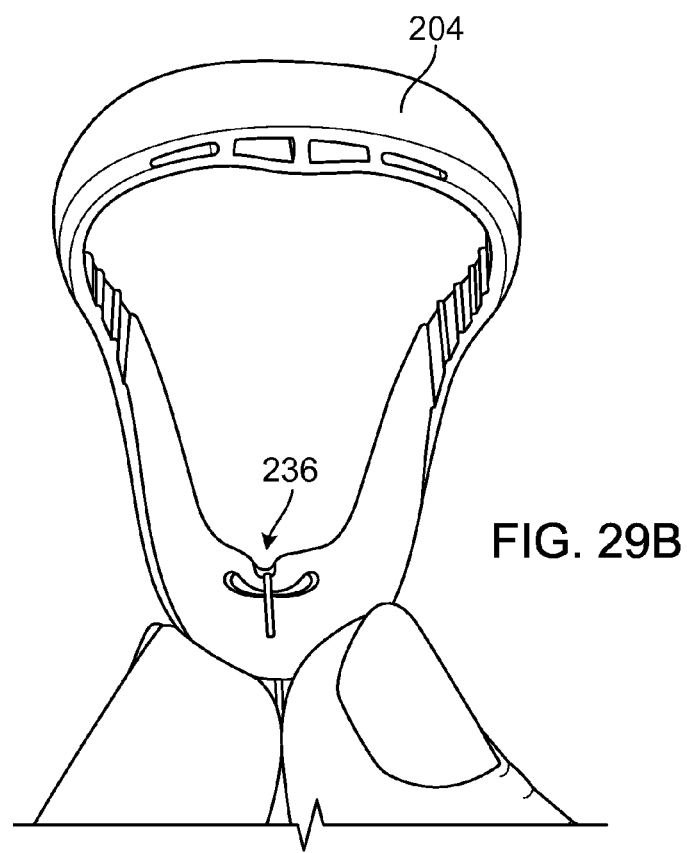

The tongue engagement element 204 includes a tensioning mechanism 236 (FIGS. 27b and 29b) that secures the tongue engagement element 204 in the user's mouth by keeping the floss member 232 under tension and thus keeping anchor 230 in place against the front of the user's lower teeth and gum. To form the tensioning mechanism 236, the front region 206 of the tongue engagement element 204 includes a bridge 238 defining an opening 240, for example, a 5 mm by 10 mm opening. The floss members 232, 234 pass through a hole 242 in front region 206, span the opening 240, and are fixed to the bridge 238. Referring to FIG. 29b, when the anchor 230 is pulled, the bridge 238 is resiliently deformed, placing the floss member 232 under tension. It takes, for example, the application of 1½ pounds of force to flex the bridge 238, with the amount of force being determined by the material, the size of the opening 240 and the thickness of the bridge 238. The floss member 234 is longer than the floss member 232 such that the floss member 234 is not placed under tension.

Figure 29C:
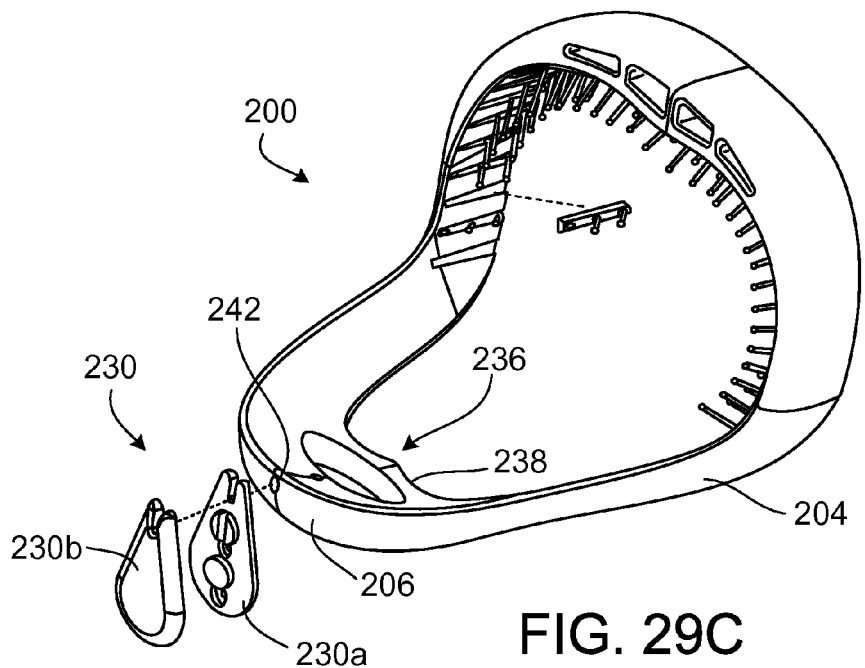
Figure 29E:
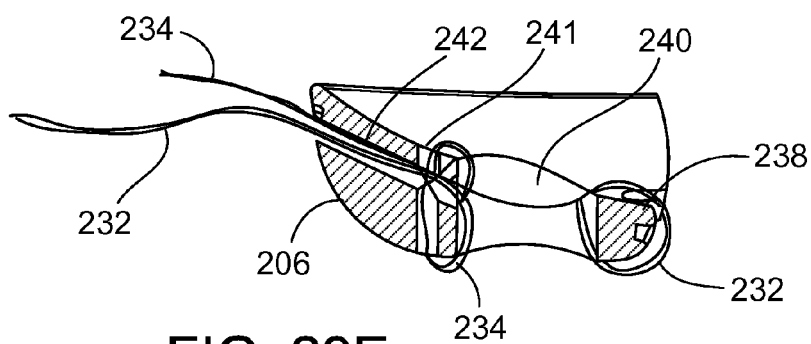
Figure 29D:
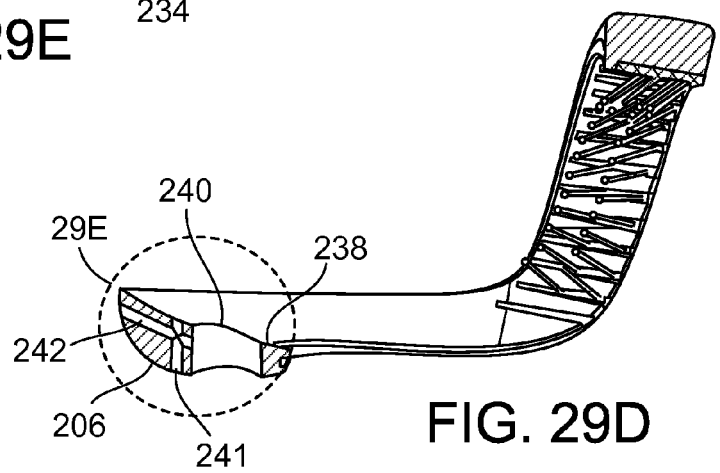

The anchor 230 can be constructed of a male tab 230a and a female tab 230b, as illustrated in FIG. 29c. The floss members 232, 234 are secured between the tabs 230a, 230b, as described below, and, as shown in FIG. 29e, secured to oral appliance 200 using girth hitches. Referring also to FIG. 29d, the front region 206 includes an additional cross hole 241 for receiving the safety floss member 234 to form a girth hitch. To attach floss member 232 to oral appliance 200, the floss member 232 is doubled over, the doubled strand is looped around bridge 238, passed through itself where doubled over, and the doubled strand threaded through hole 242. To attach floss member 234 to oral appliance 200, the floss member 234 is doubled over, the doubled strand is passed through hole 241, passed through itself where doubled over, and the doubled strand threaded through hole 242.

Figure 29F:
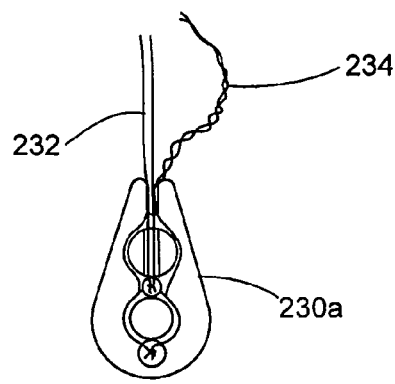
Figure 29G:
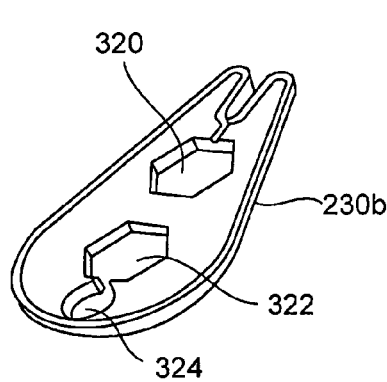
Figure 29H:
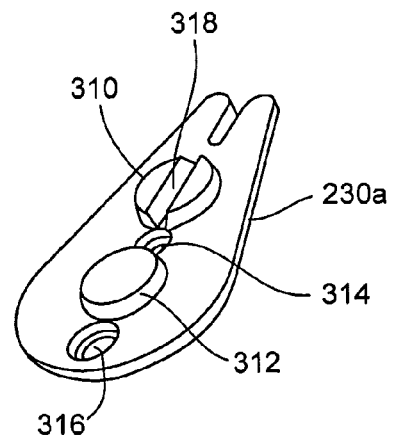
Figure 30:
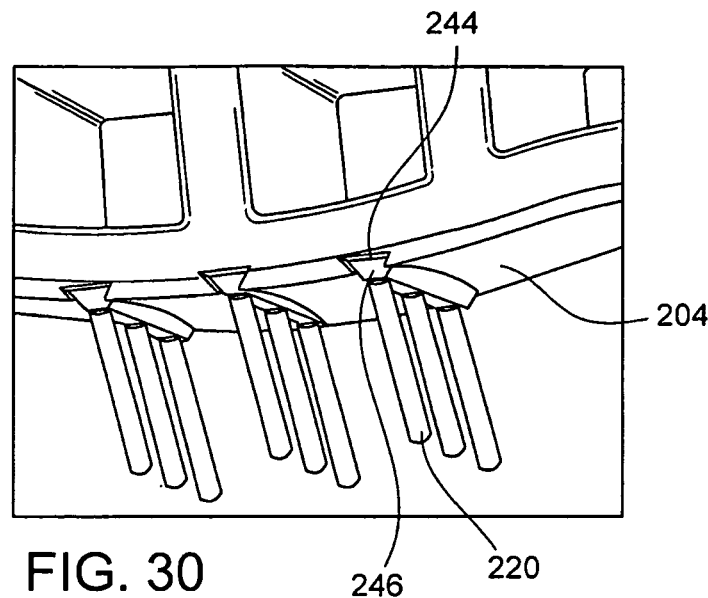

Referring to FIGS. 29f-29h, the male tab 230a of anchor 230 includes posts 310, 312 and depressions 314, 316 for receiving the floss members 232, 234. Post 310 includes a slot 318. The female tab 230b includes depressions 320, 322 that receive posts 310, 312, respectively, and a depression 324 that is aligned with depression 316 when the tabs 230a, 230b are attached. To attach the floss member 234 to the anchor 230, the free ends of the floss member 234 are knotted together, placed in depression 316, and the floss member 234 routed around the posts 312, 310. To attach the floss member 232 to the anchor 230, the free ends of the floss member 232 are knotted together, placed in depression 314, and the floss member 232 routed through the slot 318 in post 310. The female tab 230b is then adhesively bonded to the male tab 230a to secure the floss members 232, 234 to the anchor 230.

In use, the user places the tongue engagement element 204 under a front region of a tongue and over a rear region of the tongue with the side regions 210, 212 of the tongue engagement element 204 extending along the floor of the user's mouth cavity under the tongue. The user then pulls the anchor 230 to deform the bridge 238 such that there is enough length of the floss member 232 between the anchor and the front region 206 of the tongue engagement element 204 to allow the floss member 232 to be positioned between the front middle teeth, and the anchor 230 to be positioned in front of the teeth. When the anchor 230 is released, typically some deformity of the bridge 238 remains to maintain tension on the floss member 232 and to accommodate various thicknesses of different user's teeth. For example, if the front two teeth of a user are overlapped such that one tooth is sticking farther forward, for example, 2 mm, the bridge will be deflected toward the teeth by 2 mm so as to provide 2 mm more of floss length to accommodate the greater thickness as compared to a user who has straight teeth. The structures 220 engaging the tongue with the anchor 230 positioned in front of the teeth act to resist rearward motion of the tongue. The tongue engagement element 204 thus positioned does not interfere with the user's normal bite.

For safety to allow a passage for air through the user's mouth, the tongue engagement element 204 includes air vents 242 (FIG. 27a), for example four or six openings, extending through the rear region 208.

Figure 27A:
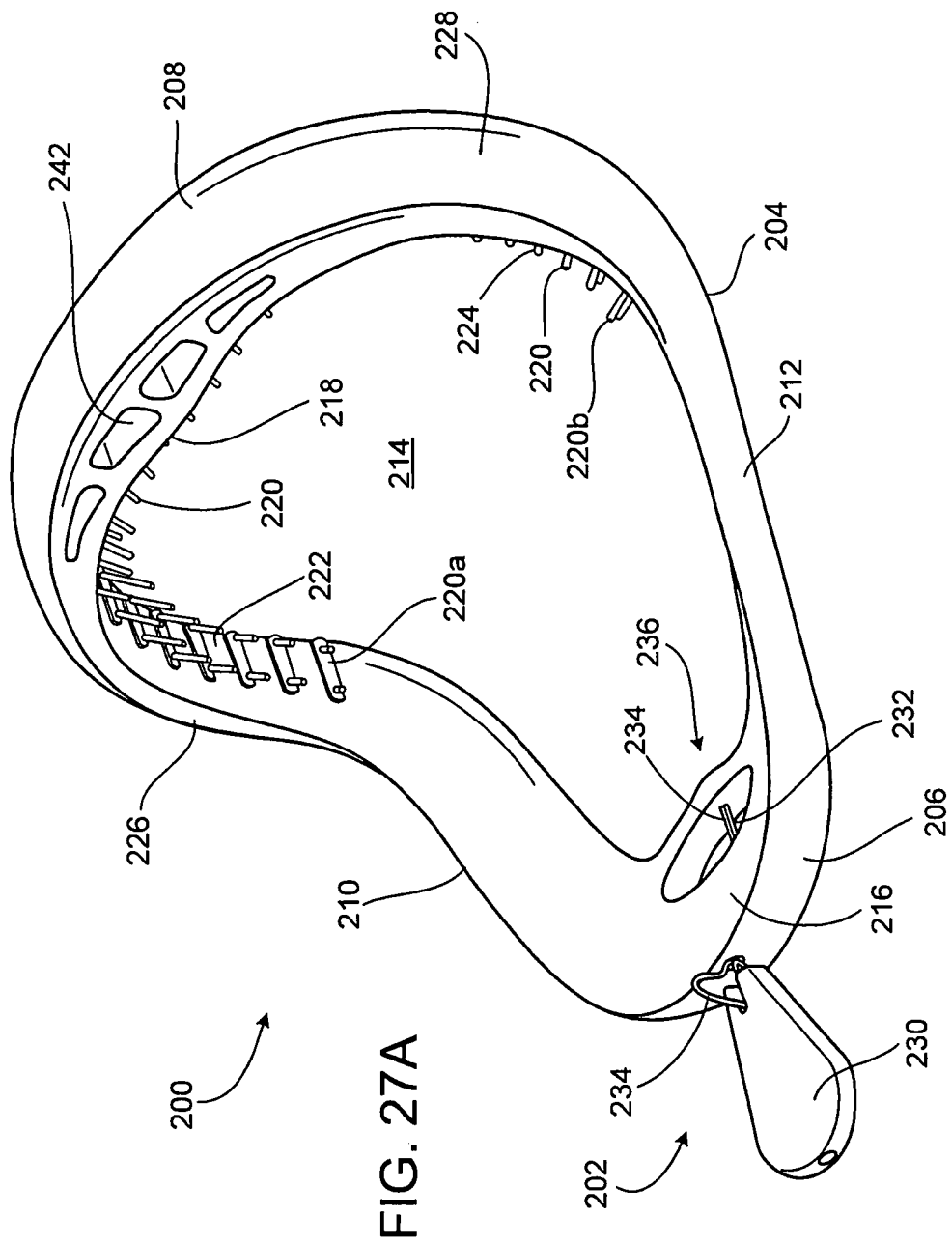
FIGS. 27a-27d are perspective, top, side and front views, respectively, of another embodiment of a tongue retaining oral appliance.
Figure 27B:
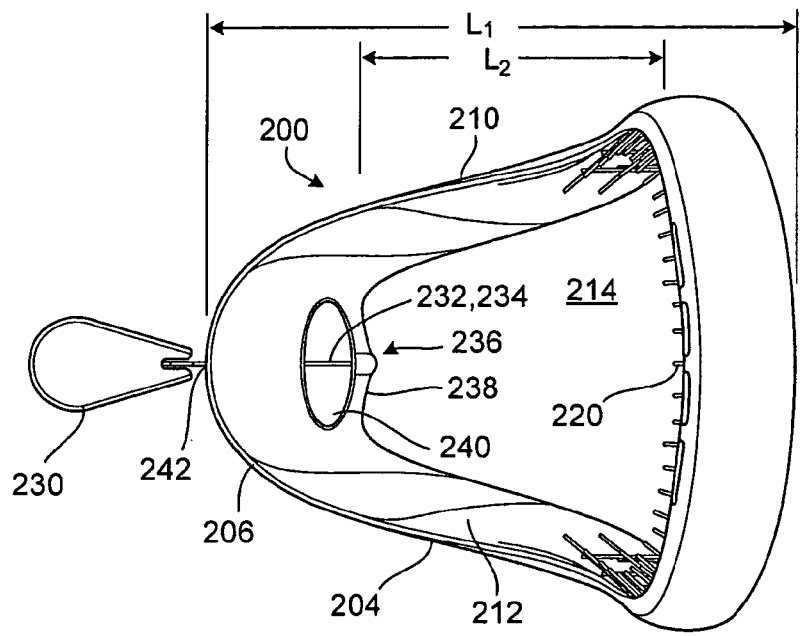
Figure 27C:
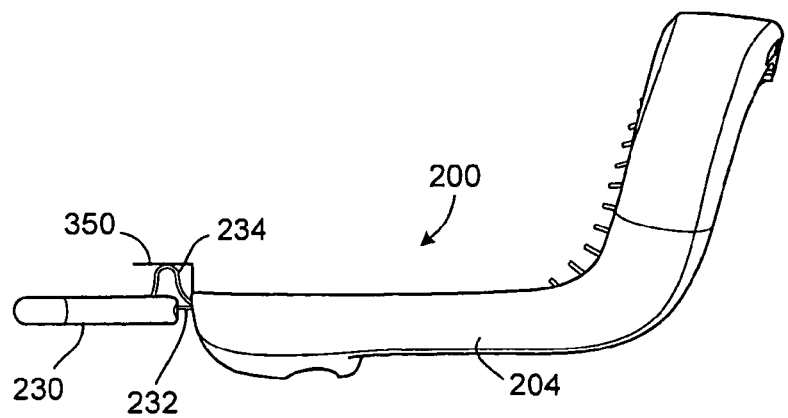
Figure 27D:
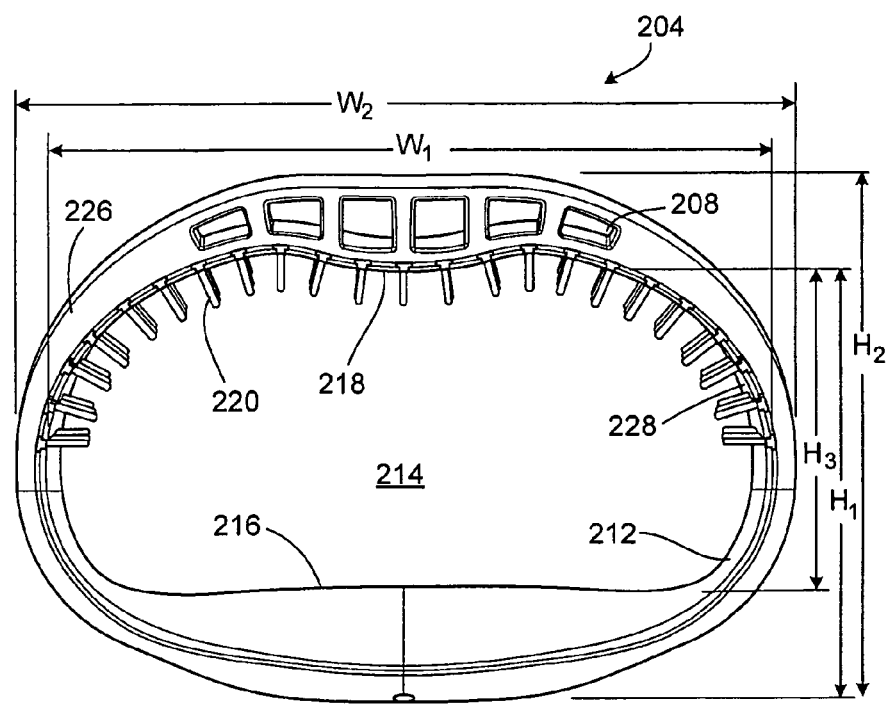

The oral appliance 200 includes one or more rows of structures 220, for example, two rows as illustrated in FIG. 27a or three rows as illustrated in FIGS. 27b-27d and 30. In the illustrated embodiment, the structures 220 are in the form of filaments. The number of rows and position of the end filament sets 220a, 220b are selected to provide optimal user comfort. The filaments 220 can be molded with the tongue engagement element 204, or, referring to FIG. 30, the tongue engagement element 204 can be molded with slots 244. Each of the slots 244 receives a spine 246 to which the filaments 220 are attached or integrally formed. The slots 244 and spines 246 of FIG. 30 have a triangular shape. Stepped, rectangular shaped slots and spines are illustrated in FIG. 27d. During manufacture, the spines 246 with attached filaments 220 are slid into the slots 244 and adhesively bonded.

Figure 31:
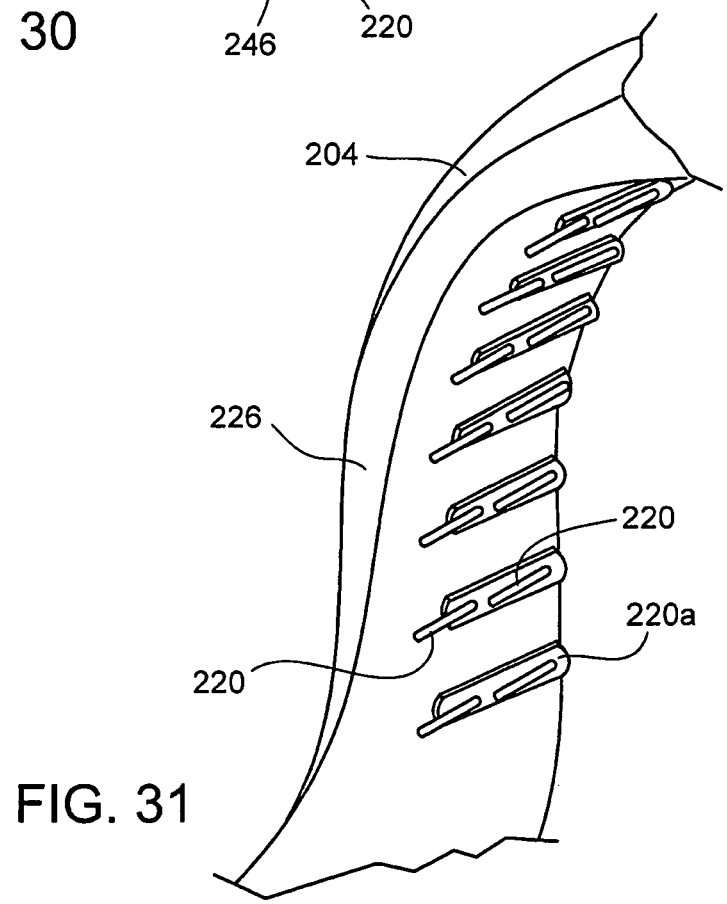

For user comfort, the filaments 220 are at an angle to the surface of the tongue (and inner surface of the element 204) and can bend to lie flat (FIG. 31) between the user's tongue and the inside surfaces 218, 222, 224 of the rear region 208 when the tongue engagement element 204 is positioned on the user's tongue. Any backward motion of the tongue relative to the tongue engagement element 204 causes the filaments 220 to flex downward and engage the tongue to resist the backward motion of the tongue. An advantage of the two row embodiment of FIG. 27a is that when the filaments lay flat they do not extend beyond the tongue engagement element 204 and are therefore less likely to provide discomfort by sticking into the tongue. It may also be advantageous to offset the filaments 220 of a filament set to provide sufficient room to allow the filaments 220 to lie flat alongside of each other.

Figure 32A:
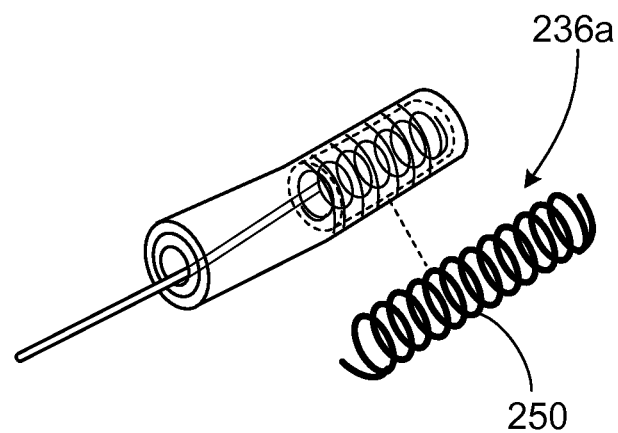
Figure 32B:
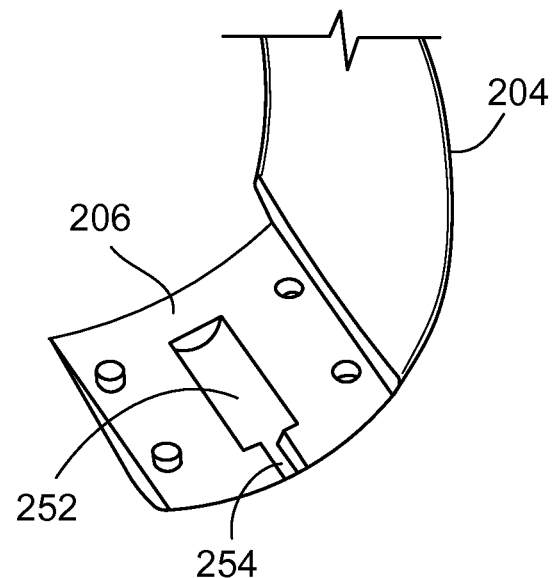
Figure 33A:
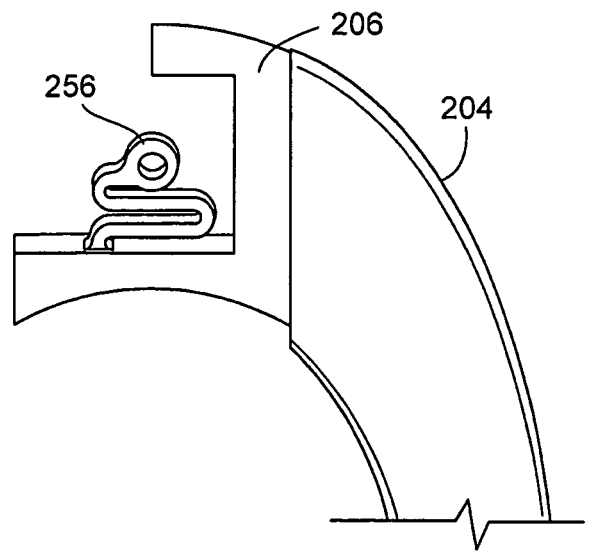
Figure 33B:
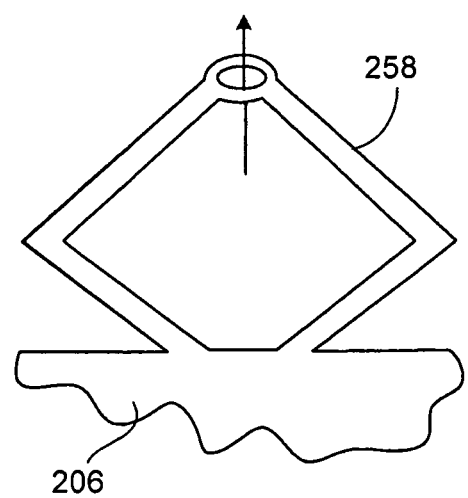

Alternatives to the tensioning mechanism 236 are illustrated in FIGS. 32 and 33. Rather than a bridge, tensioning mechanism 236a of FIGS. 32a and 32b includes a compression spring 250 that is encapsulated within the front region 206 of the tongue engagement element 204. The cut-away view of FIG. 32b shows a channel 252 and an access opening 254 for receipt of the spring 250 and the attached floss member, respectively. In use, the spring 250 maintains a constant tension of the floss member. The strength of the spring force can be controlled to provide adequate force to hold the weight of the tongue. Alternatively, as shown in FIGS. 33a and 33b, a living spring 256 or 258 can be molded into the front region 206 of the tongue engagement element 204. The living spring 258 can provide near linear force.

Figure 34A:
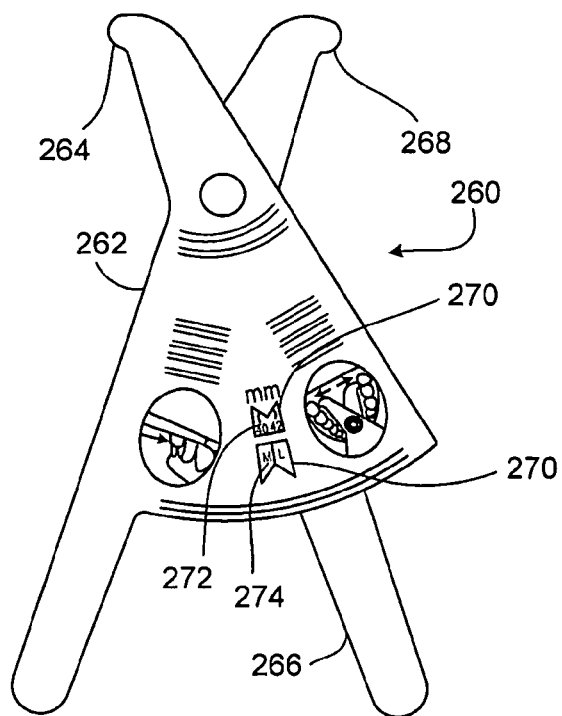
FIGS. 34a-34e illustrate a sizing tool.
Figure 34B:
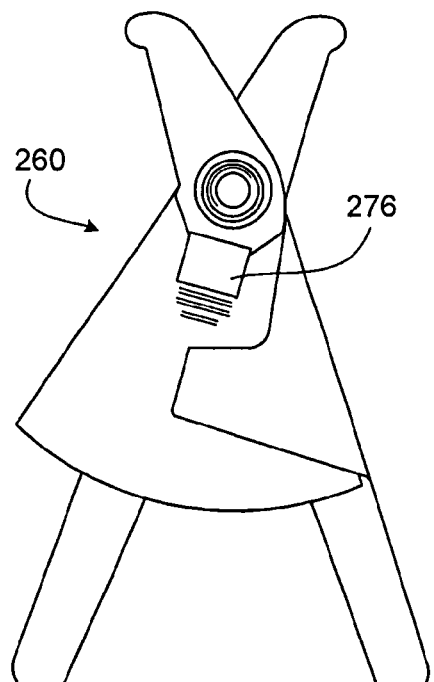
Figure 34C:
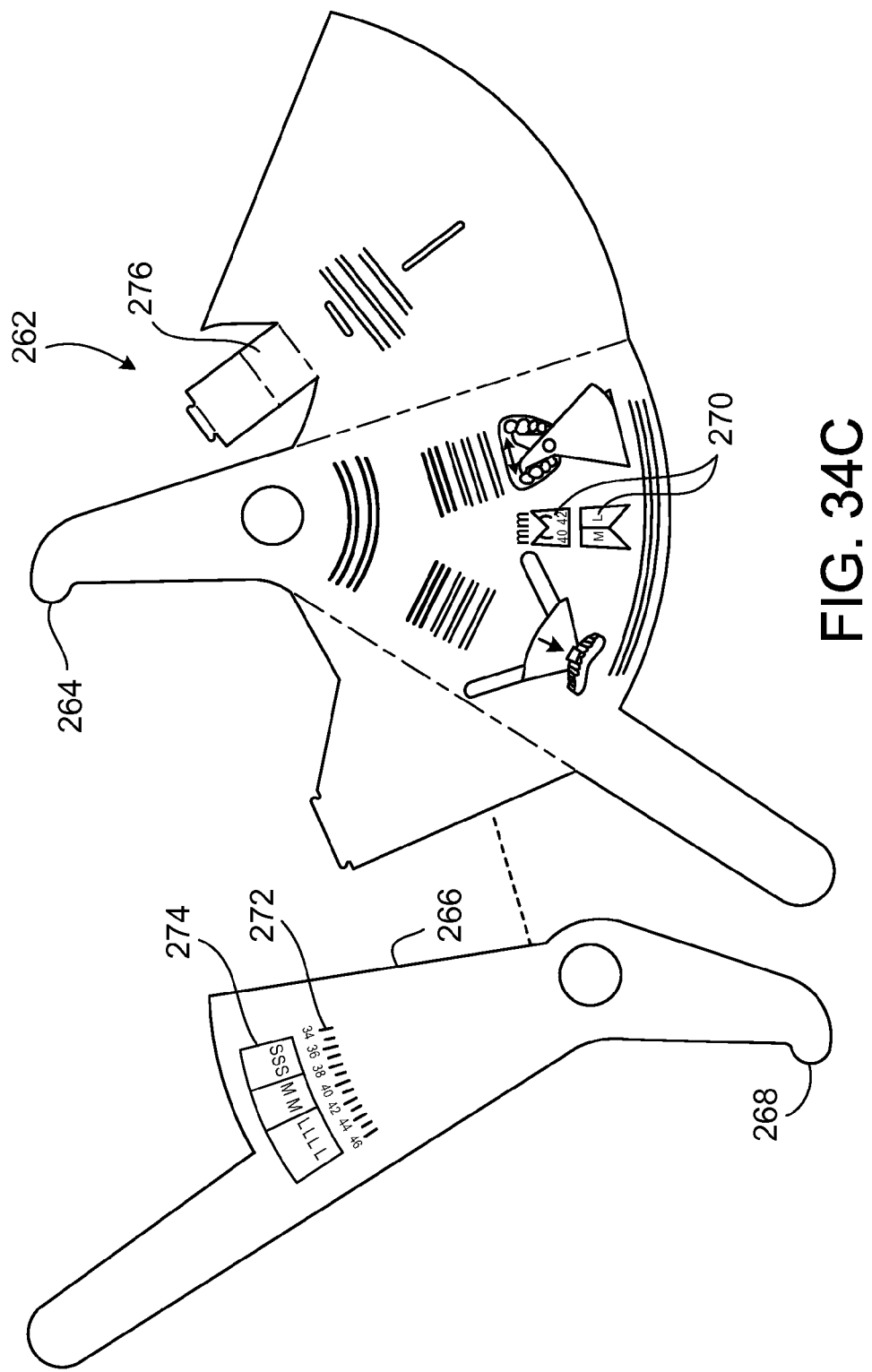

As discussed above, the oral appliance 200 can be provided, for example, in three sizes to fit mouths of different sizes. Referring to FIGS. 34a-34c, to allow a physician to determine or a user to make a self determination of the appropriate sized oral appliance 200, a sizing tool 260 is provided for measuring the spacing between the last molars if the wisdom teeth have been removed or the molars just in front of the wisdom teeth (second lower molars #18 and 31). The tool 260 has a first arm 262 with a molar contacting portion 264, and a second arm 266 with a molar contacting portion 268. The second arm 266 pivots relative to the first arm 262 to adjust the spacing between the molar engaging portions 264, 268. The first arm 262 includes windows 270, and the second arm includes size marking colors, mm marking 272 and small/medium/large markings 274, that can be seen through the windows 270. The underside of the tool 260 includes a tab 276.

Figure 34D:
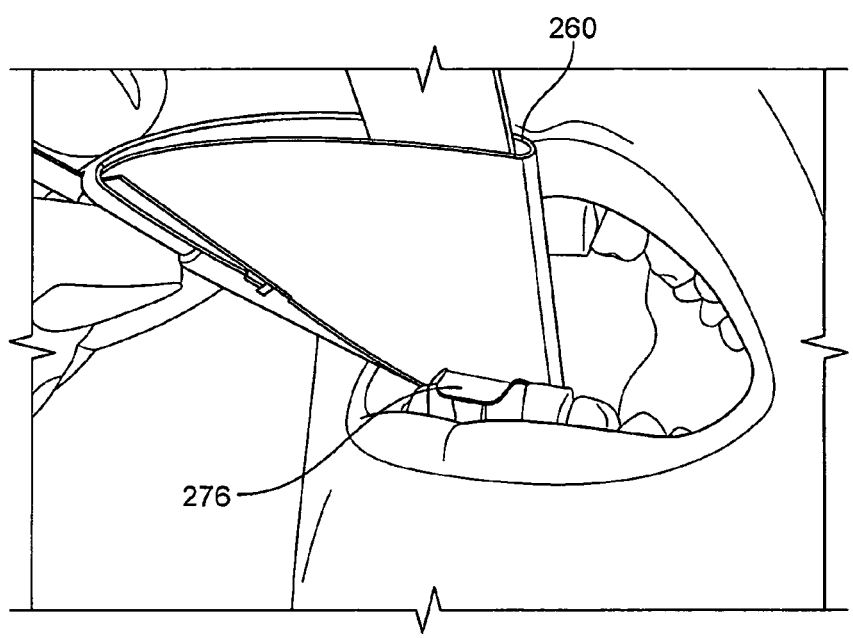
Figure 34E:
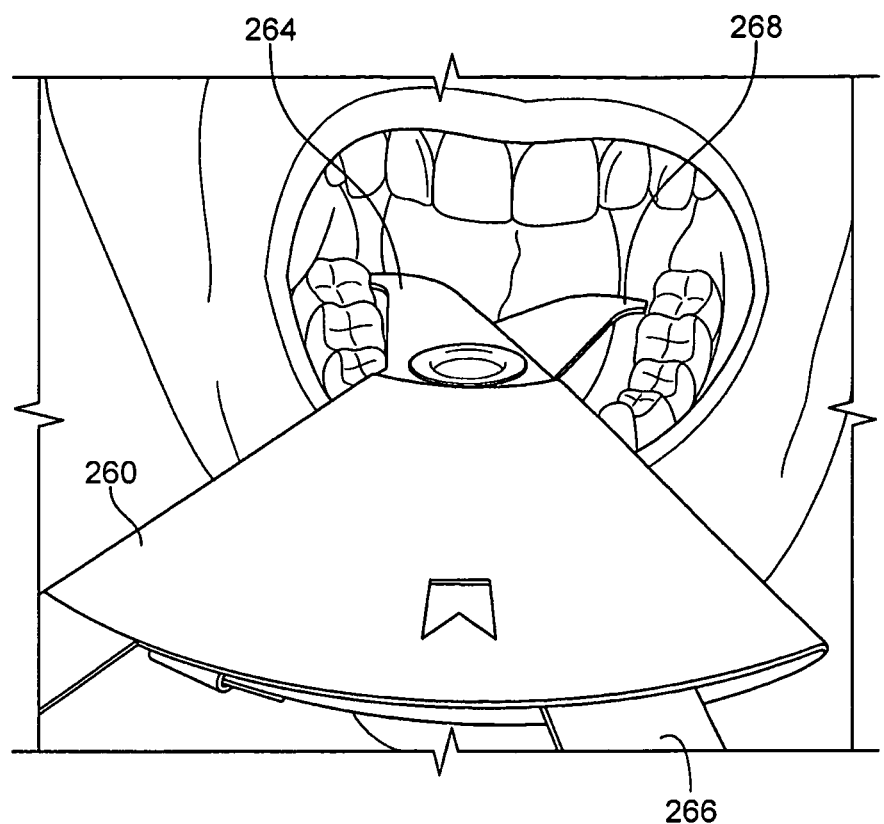
Figure 35A:
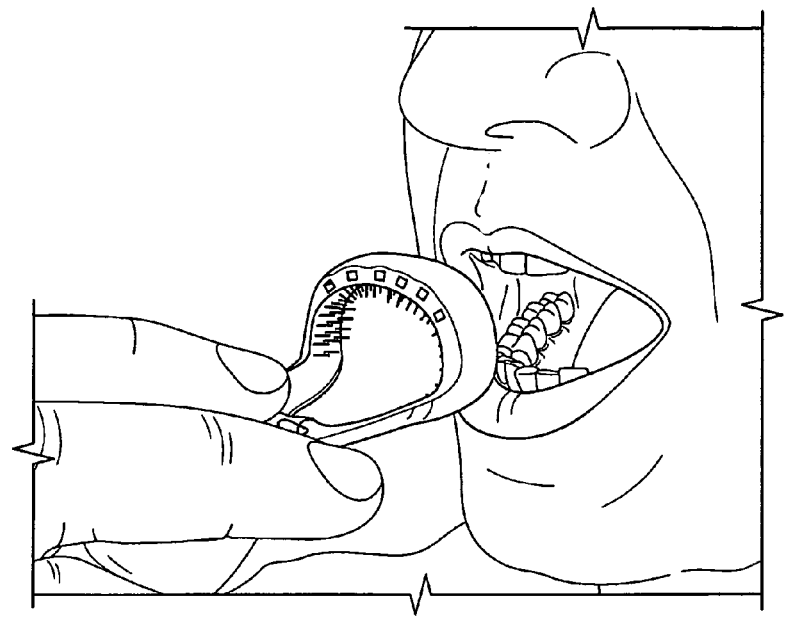
FIGS. 35a-35j illustrate placement of the tongue retaining oral appliance of FIG. 27a in a user's mouth and removal from a user's mouth.
Figure 35B:
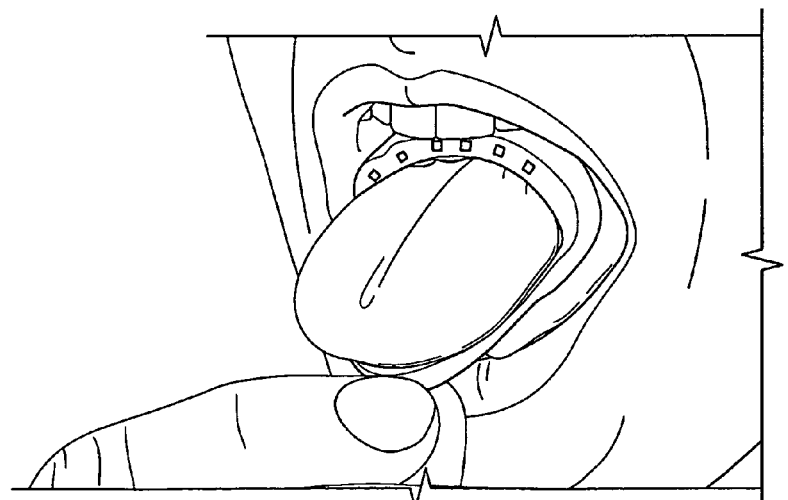
Figure 35C:
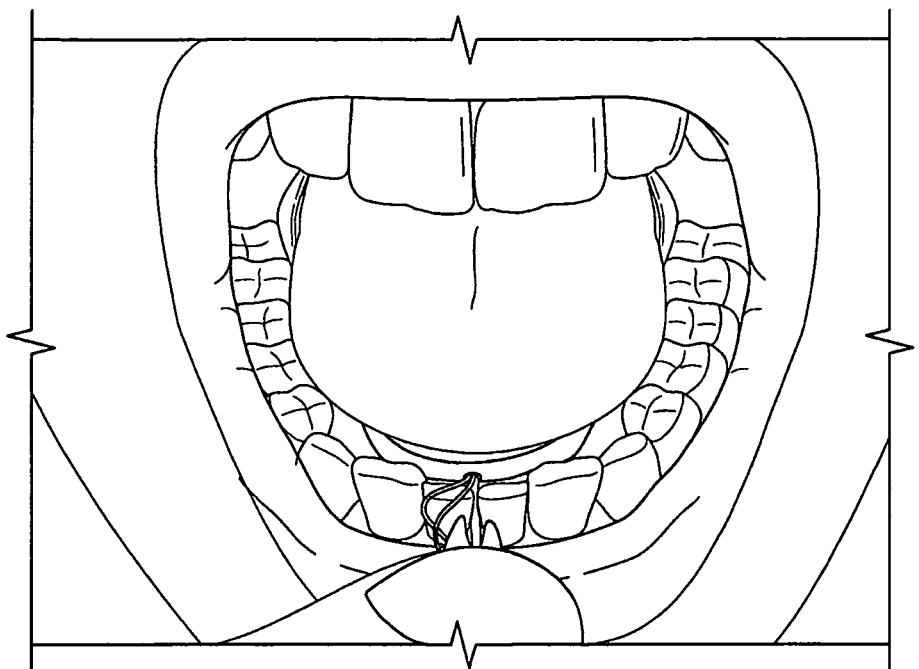
Figure 35D:
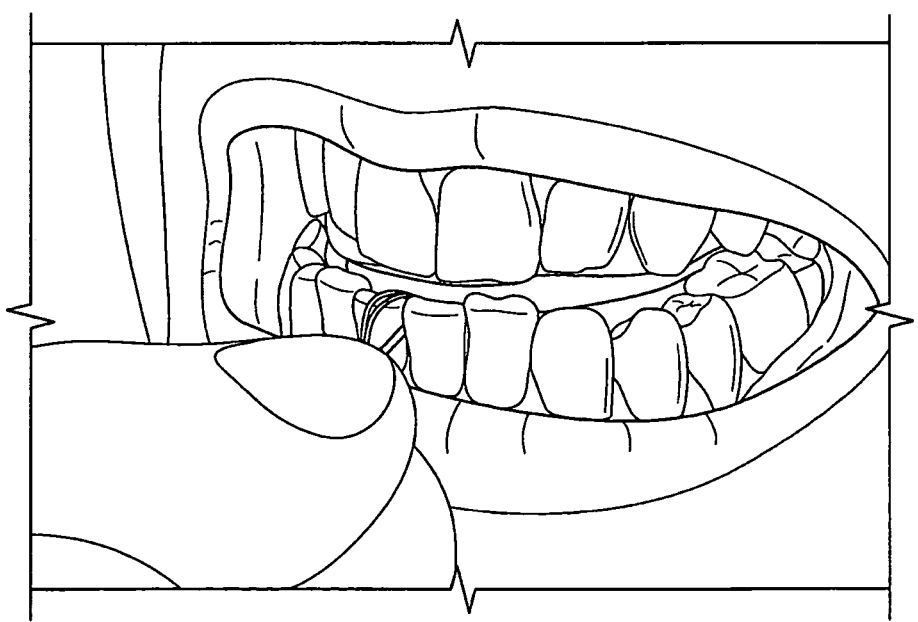
Figure 35E:
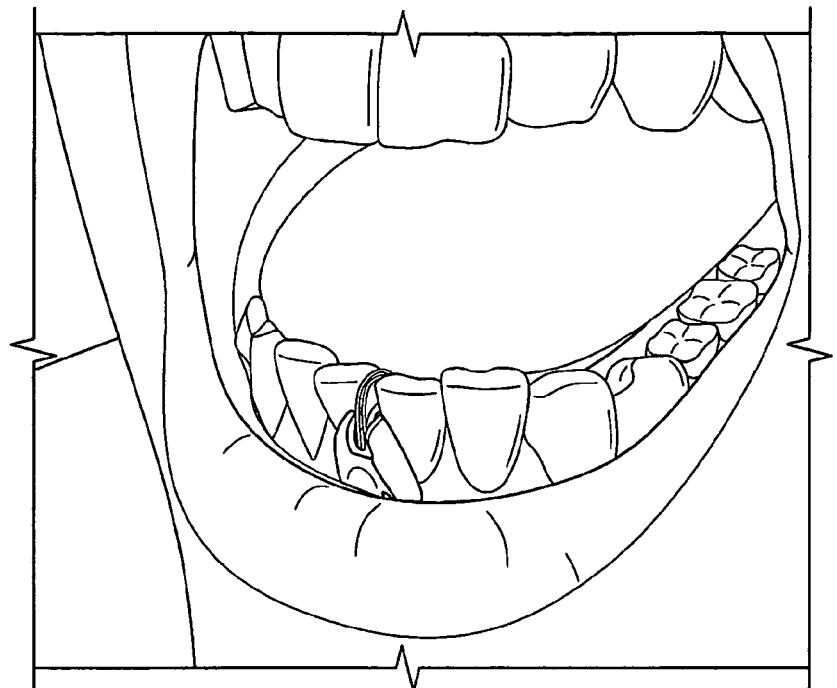
Figure 35F:
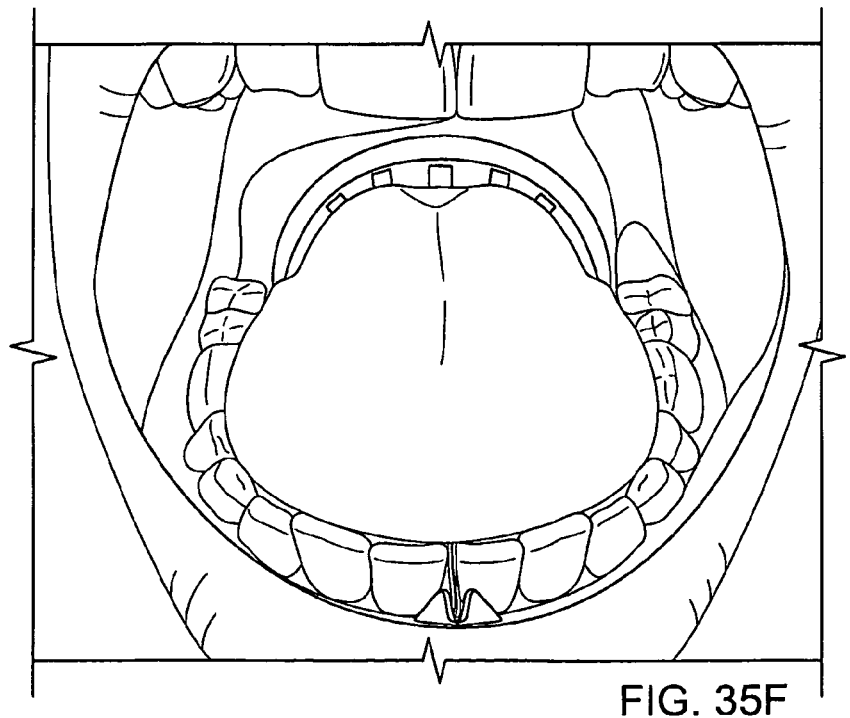
Figure 35G:
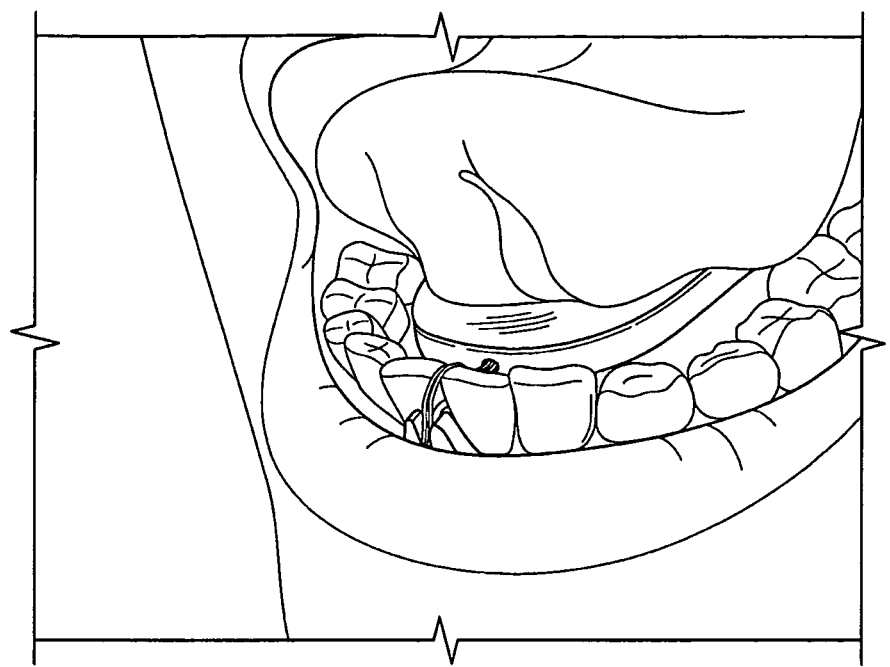
Figure 35H:
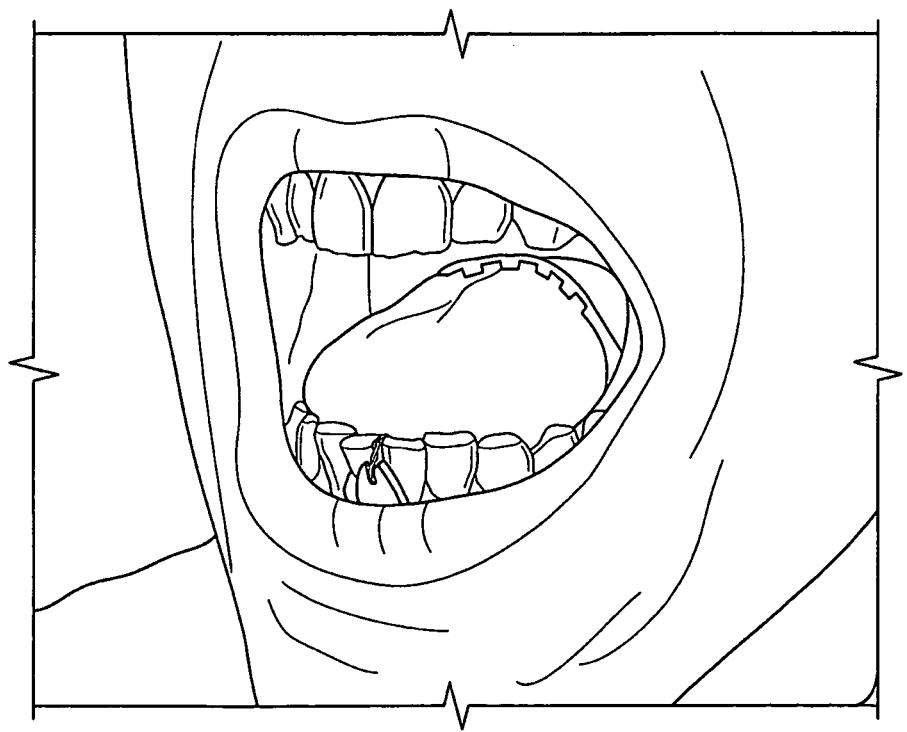

In use, referring to FIGS. 34d and 34e, the user or physician places the tab 276 against the outer surface of the lower middle teeth and spreads the arms 262, 266 until the arms touch the inside edge of the molars. The appropriate sized oral appliance 200 for the user can be read through the windows 270. Once the appropriate sized oral appliance 200 has been selected, the user places and secures the device within their mouth, as illustrated in FIGS. 35a-35d. The user inserts their tongue into the appliance 200 as far as is comfortable (FIG. 35b). The user grasps the attachment handle (anchor) 230 and slides the attachment string (floss member) 232 between their two front lower teeth (FIG. 35c-d). The position of the secured oral appliance 200 relative to the user's tongue and teeth is shown in FIGS. 35e-35h. The safety string (floss member) 234 is not between the two front teeth but rides over the tooth line. With the appliance anchored against the two front lower teeth, it is possible for the user to further adjust their tongue forward if desired and comfortable.

Figure 35I:
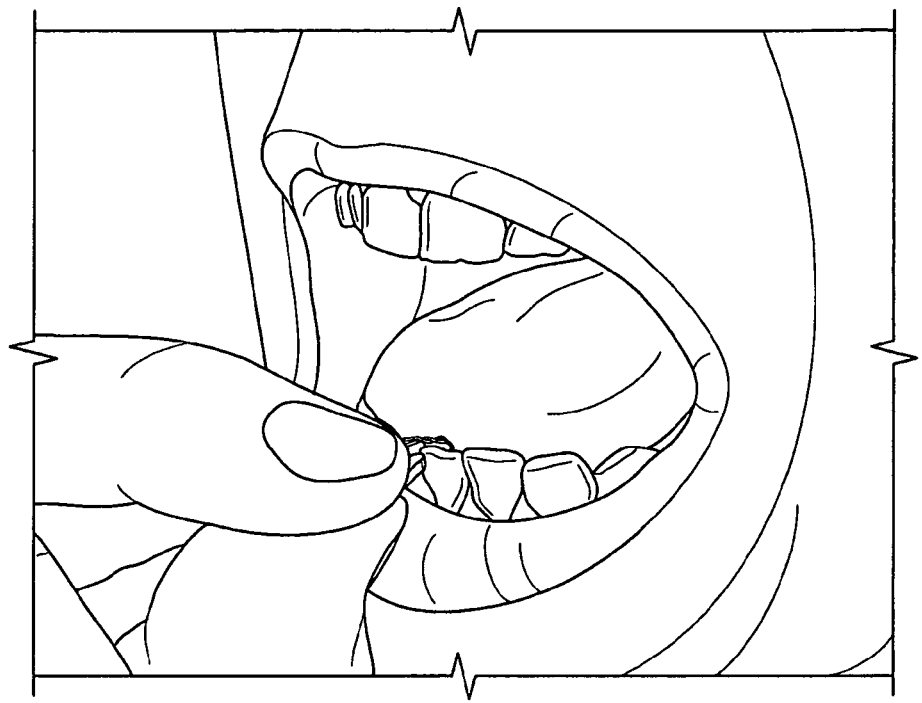
Figure 35J:
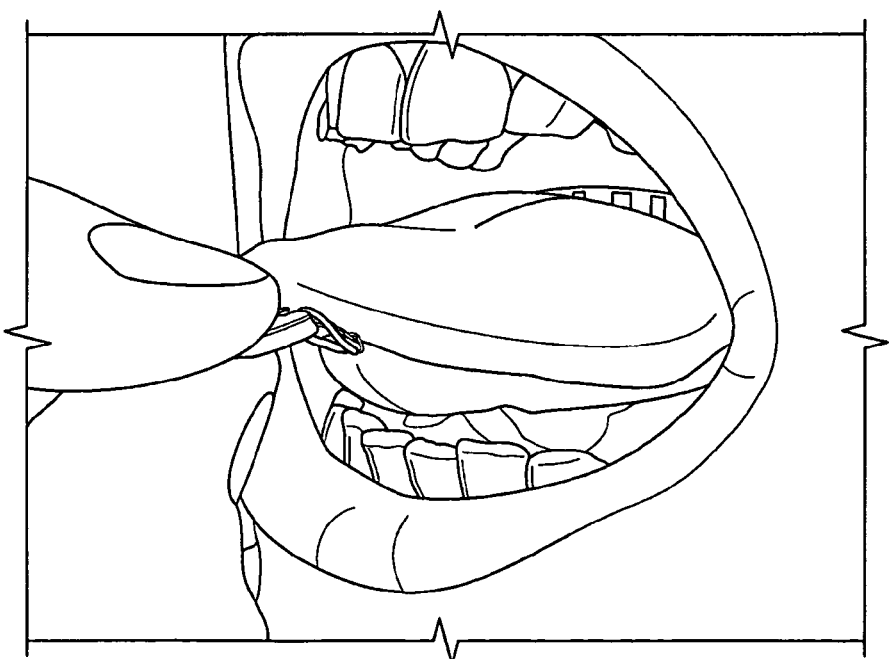

Removal of the oral appliance 200 is illustrated in FIGS. 35i and 35j. The user releases the attachment string 232 by grasping the attachment handle 230 and pulling in an upward direction. This releases the attachment string from between the two front teeth (FIG. 35i). The user uses the attachment handle 230 to pull the appliance forward out of their mouth (FIG. 35j). The user then grasps the appliance in their fingers and rotates slightly to release their tongue from the tongue engaging filaments and then removes the appliance from their mouth.

In an alternative embodiment, only the inner surfaces 222, 224 of the piers 226, 228, respectively, include tongue retaining structures 220.

Figure 36:
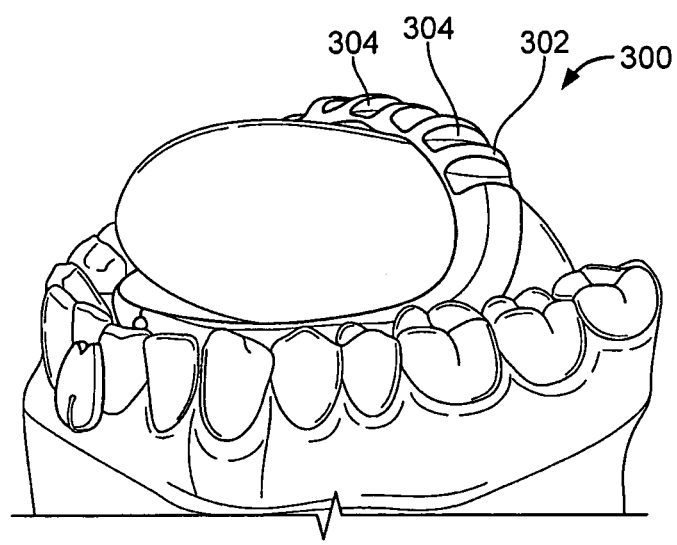
FIG. 36 illustrates an alternative embodiment of a tongue retaining oral appliance.

Rather than air vents, an oral appliance 300 (FIG. 36) has a scalloped upper surface 302 that forms air channels 304.

Where a user may have a relatively small airway or lax airway, it may be beneficial while sleeping to have the user's tongue maintained in a position forward of the tongue's normal position, for example, protruding slightly between the teeth but behind the lips, such that a larger airway is maintained. To facilitate the positioning of the oral appliance on the tongue, and thus to what extent the tongue protrudes forward of the oral appliance, a ruled member 350 (FIG. 27c) can be attached, for example, removably attached for repeated use, to the front region of the oral appliance. The user can use the ruled member 350 to repeatedly attach the oral appliance to the tongue in the desired relative position. The ruled member 350 can be applicable to all users as an aid to providing precise adjustment of posterior lingual tension to tune in the airway opening effect.

The oral appliance 200 can have the added benefit of positioning the tongue in its normal position against the palate. Normally, tongue adhesion to the palate holds one's mouth closed. In a sufferer of sleep apnea, when the tongue moves backward in the mouth, the tongue no longer adheres to the palate and the mouth can open. The oral appliance 100, by positioning the tongue against the palate, allows the necessary adhesion to be created between the tongue and the palate to hold the user's mouth closed. This can be further facilitated by adding adhesive on top of the rear region 208 to adhere the rear region 208 to the palate.

The oral appliances described above, or another device such as described in Munehiro, U.S. Publication No. 2010/0184566, that provide internal adhesion with the palate to aid in keeping a user's mouth closed, can be used to aid the functioning of a device, for example, a nasal device, that's use depends on the user's mouth being closed. Such a nasal device for treating sleep apnea is sold by Ventus Medical under the trade name PROVENT® Sleep Apnea Therapy.

The oral appliance is fabricated, for example, of a resin, Nylon 6-6, Zytel 101L available from PolyOne, part number PD101LNC01010. The floss is, for example, a PTFE material available as DenTek® Comfort Clean.

A number of embodiments of the invention have been described. Nevertheless, it will be understood that various modifications and substitutions may be made without departing from the spirit and scope of the invention. For example, retaining bands and retaining elements described above can each incorporate one or more of the retaining surfaces described.

The frames of the embodiments described herein have partial or complete engagement with the teeth, for example, engagement with just the front teeth, just the molar teeth, or with all of the teeth. Alternatively, the frame has no direct engagement with the teeth, but includes a clip, catch, or filament (floss) to attach the frame to the teeth. The frame can also provide support to the underside of the tongue, ensuring better retaining band engagement with the tongue.

An advantage of embodiments in which the retaining band wraps around the top of the user's tongue (such as illustrated in FIG. 26) is that with the tongue extending through the aperture in the oral appliance there is little chance of the user swallowing the oral appliance.

Accordingly, other embodiments are within the scope of the following claim.

What is claimed is:

1. A device for receipt in a user's mouth, comprising:
a tongue engagement element having a front region, a rear region, and side regions that define an opening for receiving a user's tongue, the side regions extending back and outward from the front region to the rear region such that the rear region is wider than the front region,
the front region having an upper surface and the rear region having a lower surface, the rear region extending upward relative to the front region such that the lower surface is spaced from the upper surface to receive the user's tongue therebetween,
the element shaped such that when placed in a user's mouth, the rear region extends over the user's tongue, the front region extends under the user's tongue, and the element fits within the lingual surfaces.

2. The device of claim 1 wherein the rear region including tongue retaining structures.

3. The device of claim 2 wherein the tongue retaining structures comprise bristles.

4. The device of claim 3 wherein the bristles comprise microfilament bristles.

5. The device of claim 1 wherein the rear region is configured to extend over the user's tongue to rest on the tongue.

6. The device of claim 1 wherein the side regions are configured to extend along the floor of the user's mouth cavity under the tongue and the rear region is generally arch shaped with tongue retaining structures to engage the sides and the top of the user's tongue.

7. The device of claim 1 wherein the rear region is generally arch shaped with piers that include tongue retaining structures.

8. The device of claim 7 wherein the rear region is configured to curve over the user's tongue to engage the sides of the user's tongue with the tongue retaining structures.

9. The device of claim 1 wherein the tongue engagement element has a length, L, that is greater than a width, W1.

10. The device of claim 1 wherein the lower surface is spaced from the upper surface at least about 13 mm.

11. The device of claim 1 wherein the front, rear, and side regions form a loop.

12. The device of claim 1 wherein the device is configured to not cover bite contacting surfaces of the user's teeth.

13. The device of claim 1 wherein the tongue engagement element has a length, L, that is greater than a width, W1, and the lower surface is spaced from the upper surface at least about 13 mm.

14. A device for receipt in a user's mouth, comprising:
a tongue engagement element having a front region, a rear region, and side regions that define an opening for receiving a user's tongue, the side regions extending back and outward from the front region to the rear region such that the rear region is wider than the front region,
the front region having an upper surface and the rear region having a lower surface, the rear region extending upward relative to the front region such that the lower surface is spaced from the upper surface to receive the user's tongue therebetween,
the element shaped such that when placed in a user's mouth, the rear region extends over the user's tongue, the front region only extends under the user's tongue, and the side regions are configured to extend along the floor of the user's mouth cavity under the tongue.

15. The device of claim 14 wherein the rear region is generally arch shaped with piers that include tongue retaining structures.

16. The device of claim 15 wherein the rear region is configured to curve over the user's tongue to engage the sides of the user's tongue with the tongue retaining structures.

17. The device of claim 15 wherein the tongue retaining structures comprise bristles.

18. The device of claim 14 wherein the rear region is configured to not extend under the user's tongue.

19. A device for receipt in a user's mouth, comprising:
a tongue engagement element having a front region, a rear region, and side regions that define an opening for receiving a user's tongue, the side regions extending back and outward from the front region to the rear region such that the rear region is wider than the front region, the front region having an upper surface and the rear region having a lower surface, the rear region extending upward relative to the front region such that the lower surface is spaced from the upper surface to receive the user's tongue therebetween, the element shaped such that when placed in a user's mouth, the rear region extends over the user's tongue and the front region only extends under the user's tongue, and an anchor and a member connecting the element and the anchor, the member configured to be positioned between two adjacent lower teeth.

20. The device of claim 19 wherein the member and the anchor are configured such that the member can reside spaced from the gum line and the anchor can reside between the user's teeth and user's lip to secure the tongue engagement element in the user's mouth.

* * * * *